United States Patent
Grant et al.

(10) Patent No.: US 11,278,269 B2
(45) Date of Patent: Mar. 22, 2022

(54) VASCULAR CLOSURE DEVICE

(71) Applicant: Vivasure Medical Limited, Galway (IE)

(72) Inventors: Peter Grant, Dangan (IE); Bartosz Pawlikowski, Moycullen (IE); Noelle Barrett, Knocknacarra (IE); Mark McGoldrick, Athlone (IE); Gerard Brett, Claregalway (IE)

(73) Assignee: Vivasure Medical Limited, Galway (IE)

( * ) Notice: Subject to any disclaimer, the term of this patent is extended or adjusted under 35 U.S.C. 154(b) by 429 days.

(21) Appl. No.: 15/598,431

(22) Filed: May 18, 2017

(65) Prior Publication Data

US 2017/0333014 A1 Nov. 23, 2017

Related U.S. Application Data

(60) Provisional application No. 62/339,638, filed on May 20, 2016, provisional application No. 62/343,573, filed on May 31, 2016.

(51) Int. Cl.
*A61B 17/00* (2006.01)
*A61B 17/12* (2006.01)
*A61B 90/00* (2016.01)

(52) U.S. Cl.
CPC .. *A61B 17/0057* (2013.01); *A61B 2017/0053* (2013.01); *A61B 2017/00615* (2013.01);
(Continued)

(58) Field of Classification Search
CPC ........ A61B 17/0057; A61B 2017/0053; A61B 2017/00615; A61B 2017/00646;
(Continued)

(56) References Cited

U.S. PATENT DOCUMENTS

| | | | |
|---|---|---|---|
| 5,759,194 A | 6/1998 | Hammerslag | |
| 2003/0163085 A1* | 8/2003 | Tanner | A61B 18/24 |
| | | | 604/95.01 |

(Continued)

FOREIGN PATENT DOCUMENTS

| | | |
|---|---|---|
| AU | 2009208049 A1 | 8/2009 |
| CN | 101389276 A | 3/2009 |

(Continued)

OTHER PUBLICATIONS

Definition of Depress at Dictionary.com, https://www.dictionary.com/browse/depress, Accessed Apr. 20, 2021, Dictionary.com Unabridged based on the Random House Unabridged Dictionary, Random House, Inc. (Year: 2021).*

(Continued)

Primary Examiner — Kathleen S Holwerda
Assistant Examiner — Kankindi Rwego
(74) Attorney, Agent, or Firm — Choate, Hall & Stewart LLP; William R. Haulbrook; Peter A. Flynn

(57) ABSTRACT

Described herein are systems, devices, and methods for closing a perforation in any hollow vessel associated with a mammalian surgical procedure, for example a device for sealing an aperture in a tissue, the device comprising an implant and a delivery shaft configured to engage the implant, the delivery shaft comprising (i) a retaining sleeve, (ii) a release sleeve, and (iii) a handle coupled to the delivery shaft.

23 Claims, 41 Drawing Sheets

(52) U.S. Cl.
CPC .............. *A61B 2017/00646* (2013.01); *A61B 2017/00778* (2013.01); *A61B 2017/12054* (2013.01); *A61B 2090/0811* (2016.02)

(58) Field of Classification Search
CPC ........... A61B 2017/00778; A61B 2017/12054; A61B 2090/0811; A61B 17/3468; A61B 2017/347; A61B 18/00; A61B 2018/0091; A61B 2018/00916; A61B 17/1204; A61B 2017/1205; A61F 2/95; A61F 2/9517; A61F 2/01; A61F 2/011; A61F 2/24; A61F 2/2427; A61F 2/243; A61F 2/2433; A61F 2/2436; A61F 2/2439
See application file for complete search history.

(56) References Cited

U.S. PATENT DOCUMENTS

| | | | | |
|---|---|---|---|---|
| 2007/0123816 | A1* | 5/2007 | Zhu | A61B 17/0057 604/57 |
| 2010/0087811 | A1* | 4/2010 | Herrin | A61B 17/0057 606/40 |
| 2012/0078352 | A1* | 3/2012 | Wang | A61F 2/2427 623/2.11 |
| 2014/0018846 | A1 | 1/2014 | Grant et al. | |

FOREIGN PATENT DOCUMENTS

| | | |
|---|---|---|
| CN | 102802538 A | 11/2012 |
| CN | 104739461 A | 7/2015 |
| CN | 105286928 A | 2/2016 |
| EP | 2697721 B1 | 9/2019 |
| WO | WO-2007/078812 A2 | 7/2007 |
| WO | WO-2010/118312 A2 | 10/2010 |
| WO | WO-2010/151510 A1 | 12/2010 |
| WO | WO-2011/027003 A1 | 3/2011 |
| WO | WO-2012/065189 A1 | 5/2012 |
| WO | WO-2013/128292 A2 | 9/2013 |

OTHER PUBLICATIONS

International Search Report, PCT/EP2017/062035 (Vascular Closure Device filed May 18, 2017), ISA/EPO, 5 pages, Oct. 19, 2017.
Written Opinion, PCT/EP2017/062035 (Vascular Closure Device filed May 18, 2017), ISA/EPO, 8 pages, Oct. 19, 2017.

* cited by examiner

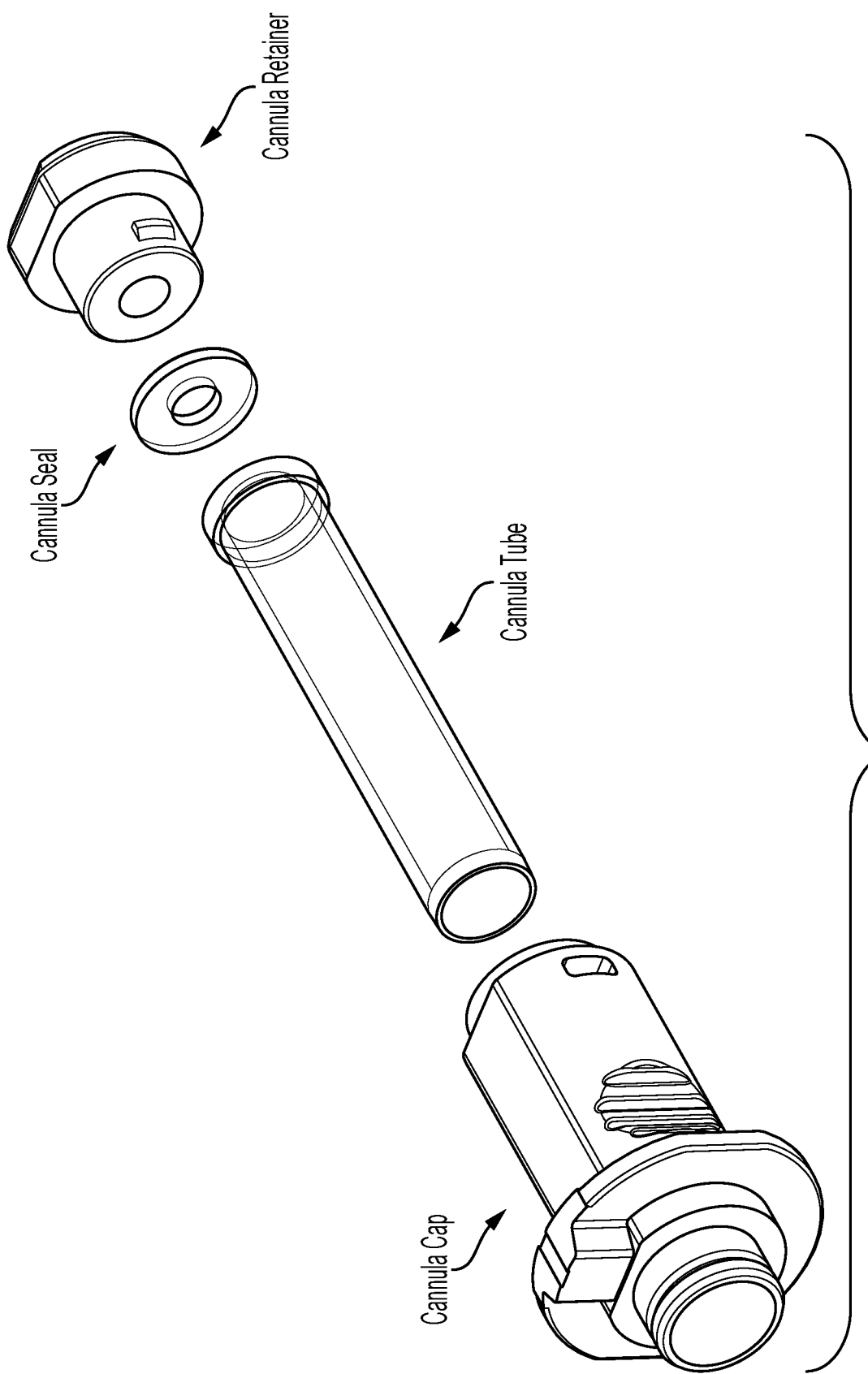

VASCULAR CLOSURE DEVICE

CROSS-REFERENCE TO RELATED APPLICATIONS

This application claims the benefit of priority to U.S. Provisional Patent Application No. 62/339,638, filed May 20, 2016 and U.S. Provisional Patent Application No. 62/343,573, filed May 31, 2016, each of which is incorporated herein its entirety by reference thereto.

FIELD OF INVENTION

The present invention relates generally to closure systems, devices, and methods for use in surgical procedures.

BACKGROUND

Minimally invasive procedures are continually increasing in number and variation in part because such techniques offer an immediate advantage over more traditional, yet highly invasive surgeries. Endoscopic surgery, for example, uses one or more scopes inserted through small incisions for diagnosing and treating disease. In particular, endovascular surgery gives access to many regions of the body, such as the heart, through major blood vessels. Typically, the technique involves introducing a surgical instrument percutaneously into a blood vessel, such as, for example, the femoral artery. The currently emerging percutaneous endovascular procedures include aortic valve replacement, mitral valve repair, abdominal and thoracic aneurysm repair, and tricuspid valve replacement. Other procedures requiring access to the femoral artery include coronary, carotid, and cerebral angiographic procedures. Other procedures may require venous access, such as intravenous antibiotic treatment or long-term intravenous feeding for nutritional support.

Other examples of a minimally invasive procedure include NOTES (Natural Orifice Translumenal Endoscopic Surgery) based surgery, e.g., transgastric, transvesical, and transcolonic approaches.

A key feature of these minimally invasive surgical procedures is the forming of a temporary pathway, usually an incision or dilated perforation, to the surgical site. For example, in the emerging percutaneous endovascular procedures, an access site (e.g., incision, puncture hole, or perforation) ranging from approximately 10 to 30 French units is formed as a temporary pathway to access the target site. Various instruments, such as procedural sheaths, guidewires and catheters, are inserted through the access site, as well as specialized medical instruments, such as, balloon catheters, and stents.

Currently, these large (10 to 30 French (F)) puncture holes (or perforations) or access sites are routinely created after surgical cut down to the blood vessel, and post-procedure are closed via cut-down surgical repair. This method is very invasive and fraught with complications. Accordingly, the rapid development of percutaneous endovascular surgery, of which interventional radiology and cardiology are a major component, has led to the need for instrumentation to minimize the risk of complications associated with closing the access site after a procedure.

SUMMARY

In one aspect of the invention, the invention is directed to a device for sealing an aperture in a tissue, the device comprising: an implant configured to seal the aperture when positioned adjacent to the aperture and a delivery shaft configured to engage the implant to allow the implant to be maneuvered into sealing engagement with a distal surface of the tissue, the delivery shaft comprising: (i) a retaining sleeve comprising a locking projection engagable with the locking recess of the implant to secure the implant to the delivery shaft; (ii) a release sleeve axially slideable relative to the retaining sleeve between a first axial position in which the release sleeve is configured to maintain locking engagement between the locking recess of the implant and the locking projection of the retaining sleeve, and a second axial position in which the release sleeve permits the locking projection of the retaining sleeve to disengage the locking recess of the implant; and (iii) a handle coupled to the delivery shaft; and (a) a sheath cam moveable between a first position and second position relative to the handle, and (b) a sheath carriage connected to a sheath. In certain embodiments, the device is configured such that movement of the sheath cam from the first position to the second position (e.g., by rotation movement) causes (x) movement of the sheath carriage relative to the handle, causes (y) the movement of one end of the sheath into the handle, and causes (z) exposure of the implant in the vessel in an atraumatic way.

In certain embodiments, the interlocking projection is one of plurality of interlocking projections configured to engage a respective plurality of interlocking recesses of the implant.

In certain embodiments, the projection is biased toward a flared position such that movement of the release sleeve from the first axial position to the second axial position causes the interlocking projection to flare away from and out of engagement with the interlocking recess of the implant.

In certain embodiments, the device comprises: an actuator moveable between a first position and second position relative to the handle, wherein the device is configured such that (a) movement of the actuator from the first position to the second position (e.g., rotation movement) causes (a) a change in the position of two components of the implant relative to each other, and causes (b) the delivery shaft to release the implant.

In certain embodiments, the delivery shaft and/or handle comprise a plurality of graphical markings and/or engravings (e.g., alphanumeric markings) indicative of an actuating sequence for use of the device (e.g., numbering to guide the user in the use of the device).

In certain embodiments, the delivery shaft and/or sheath comprise a plurality of graphical markings and/or engravings indicating sheath penetration (e.g., depth).

In certain embodiments, the implant is formed of a polymer adapted to remain shelf stable and functional for sealing after terminal sterilization.

In certain embodiments, the polymer is adapted to remain shelf stable and functional for sealing after terminal sterilization using at least one of (a) ethylene oxide, (b) electron-beam, (c) gamma irradiation, and (d) nitrous oxide.

In certain embodiments, the polymer is biodegradable.

In certain embodiments, the polymer comprises Polydioxanone, Poly-L-lactide, Poly-D-lactide, Poly-DL-lactide, Polyglycolide, ε-Caprolactone, Polyethylene glycol, or combinations of these.

In certain embodiments, the polymer comprises polydioxanone.

In certain embodiments, the device is configured to seal a perforation in a hollow vessel.

In certain embodiments, the implant includes an intraluminal portion configured to form a seal with the perforation by contacting an intraluminal surface of the hollow vessel.

In certain embodiments, the implant includes an extra-luminal portion configured to extend outside the hollow vessel, the delivery shaft being configured to engage the implant via the extra-luminal portion.

In certain embodiments, the implant comprises a flexible wing extending outwardly from a base portion.

In certain embodiments, the device is configured to be guided over a guidewire.

In certain embodiments, the implant is formed at least in part of a material having an inherent viscosity in a range from 0.5 to 7.0 dl/g.

In certain embodiments, the implant comprises a flexible wing having a diameter greater than a diameter of the aperture in the tissue.

In certain embodiments, the implant comprises a distal foot portion, a flexible wing, and a recessed surface disposed in the distal foot portion and into which the flexible wing is positioned and crimped to provide an effective fluid seal between the foot portion and the flexible wing.

In certain embodiments, the crimping is achieved using at least one of (a) mechanical, (b) chemical, and (c) thermal methods.

In certain embodiments, the implant comprises: a flexible wing; and a foot including a distal portion configured to be disposed distally of the flexible wing when the implant is positioned to seal the aperture and a proximal neck configured to extend away from the aperture and proximally away from the aperture.

In certain embodiments, the distal portion of the foot has a length this is greater than a diameter of the aperture.

In certain embodiments, the proximal neck is flexible relative to the distal portion of the foot.

In certain embodiments, the proximal neck extends distally along an axis relative to an upper surface of the distal portion of the foot at an angle that is within the range from 10° to 70°.

In certain embodiments, the distal portion of the foot is configured to reinforce the flexible wing to facility sealing of the aperture.

In certain embodiments, the implant comprises a base portion and a pin moveable relative to the base portion between a first position and a second position, wherein the pin in the second position is configured to extend outwardly from the base to provide a safety against the base being fully pushed or pulled distally through the aperture to be sealed.

In certain embodiments, the implant includes a guide channel configured to receive a guide wire.

In certain embodiments, the pin is configured to block the guide channel when the pin is in the second position.

In certain embodiments, the pin is configured to leave the guide channel open when the pin is the second position.

In certain embodiments, the base includes a cavity configured to allow sealing of the guide channel via coagulation after removal of a guidewire from the guide channel.

In certain embodiments, the device further comprises: a loading funnel configured to fold the implant into an elongated folded configuration to permit the wing to pass through a procedural sheath when the delivery shaft maneuvers the implant into a location of the aperture to be sealed.

In certain embodiments, the loading funnel includes: a tapered portion configured to progressively fold the implant into the folded configuration when the implant is maneuvered through the tapered portion in a proximal direction; and a narrowed portion configured to receive the implant with the flexible wing in the folded configuration when the implant is maneuvered further in the proximal direction and proximally beyond the tapered portion.

In certain embodiments, the tapered portion comprises a frustoconical conical portion and the narrowed portion comprises a cylindrical portion.

In certain embodiments, the frustoconical portion and the cylindrical portion are non-concentric.

In certain embodiments, the narrowed portion comprises a cannula configured receive the implant with the wing in the folded configuration and that can be detached from the remainder of the loading funnel.

In certain embodiments, the device further comprises: a packaging having a proximal and a distal end, wherein the delivery shaft, the implant, and the loading funnel are disposed in the packaging such that the delivery shaft extends distally through the narrowed portion of the funnel and into the tapered portion, where the delivery shaft is coupled to the implant, and the loading funnel is held in the packaging such that proximal movement of the delivery shaft relative to the package causes, sequentially, (a) proximal movement of the implant through the tapered portion to progressively fold the implant into the folded configuration, (b) proximal movement of the implant into the cannula, and (c) separation of the cannula, with the implant disposed therein, from the remainder of the loading funnel.

In certain embodiments, the implant is held in the tapered portion by the delivery shaft a location.

In certain embodiments, the device further comprises a handle coupled to the delivery shaft, the handle being disposed in the packaging.

In certain embodiments, the cannula is configured to access multiple forms of introducer sheaths.

In another aspect of the invention, the invention is directed to a method of using the device described above, comprising: loading the implant in to the cannula at the time of a surgery in which the implant is used; and inserting the cannula into a proximal access of a procedural sheath in order to introduce the implant in the folded configuration into the procedural sheath.

In another aspect of the invention, the invention is directed to a device for sealing an aperture in a tissue, the device comprising: a sealing member configured to seal the aperture when positioned adjacent to the aperture; and a delivery device releasably coupleable to the sealing member such that the delivery device is configured to position the sealing member adjacent to the aperture, wherein the sealing member comprises a passageway configured to receive a guidewire to guide the sealing member to the aperture, the sealing member configured to seal the passageway after complete removal of the guidewire from the passageway; and a delivery shaft configured to engage the implant to allow the implant to be maneuvered into sealing engagement with a distal surface of the tissue, the delivery shaft comprising: (i) a retaining sleeve comprising a locking projection engagable with the locking recess of the implant to secure the implant to the delivery shaft; (ii) a release sleeve axially slideable relative to the retaining sleeve between a first axial position in which the release sleeve is configured to maintain locking engagement between the locking recess of the implant and the locking projection of the retaining sleeve, and a second axial position in which the release sleeve permits the locking projection of the retaining sleeve to disengage the locking recess of the implant; and (iii) a handle coupled to the delivery device; and (a) a sheath cam moveable between a first position and second position relative to the handle, and (b) a sheath carriage connected to a sheath, wherein the device is configured such that movement of the sheath cam from the first position to the second position (e.g., rotation movement) causes (x) movement of the sheath carriage relative to the handle, causes (y) the movement of one end of the sheath into the handle, and causes (z) exposure of the implant in the vessel in an atraumatic way.

In another aspect of the invention, the invention is directed to a device for sealing an aperture in a tissue, the device comprising: a sealing member configured to seal the aperture when positioned adjacent to the aperture; and a delivery device releasably coupleable to the sealing member such that the delivery device is configured to position the sealing member adjacent to the aperture, wherein the sealing member comprises a passageway configured to receive a guidewire to guide the sealing member to the aperture, the sealing member configured to seal the passageway after complete removal of the guidewire from the passageway.

In certain embodiments, the sealing member comprises a base portion and a moveable member that is moveable between a first position and a second position relative to the base portion.

In certain embodiments, the sealing member is configured such that movement of the moveable member from the first position to the second position causes occlusion of the passageway in order to seal the passageway after removal of the guidewire from the passageway.

In certain embodiments, the delivery device is configured to move the moveable member from the first position to the second position.

BRIEF DESCRIPTION OF THE DRAWINGS

FIG. 12B depicts an image of an exploded view of a cannula assembly including a cannula cap, a tube, a seal, and a retainer.

DETAILED DESCRIPTION

As described herein, example embodiments of the present invention provide surgical closure systems, devices, and methods. As such, provided systems, devices, and methods are useful for closing a perforation (e.g., a hole, puncture, tear, rip, or cut, etc.) in any hollow vessel associated with a mammalian surgical procedure. One of ordinary skill in the art will appreciate that the systems, devices, and methods are useful for closing a perforation in any lumen of a mammal, including, for example, the gastrointestinal tract (e.g., the stomach, intestines, colon, etc.), heart, peritoneal cavity, esophagus, vagina, rectum, trachea, bronchi, or a blood vessel.

Although certain figures and embodiments relate to use of systems and devices for closure of a perforation associated with vascular surgery, one of ordinary skill in the art will appreciate that components of a provided device are not size dependent (e.g., are scalable) and are therefore useful for closure of any perforation in a lumen of a mammal.

Some embodiments of the present invention are directed to a closure system, device, and method of percutaneous closure of an arteriotomy following an endovascular/intra-arterial procedure.

One of ordinary skill in the art will recognize that many mammalian lumina are comprised of one or more friable tissues. Thus, a common difficulty associated with surgical closure of a perforation in such lumina is that suture material, used in typical closure systems, tends to cause tears in the friable tissue. Such tearing of the luminal tissue impedes healing and causes scarring. Indeed, such tearing of the friable tissues of the internal lumina of blood vessels can lead to scarring, dislodgment of tissue particles, blockage, or even eventual death of the patient. In view of the fragile nature of luminal tissues, an aspect of example embodiments of the present invention is to provide systems, devices, and methods that allow seal to be formed closure of a tissue perforation in a reliable manner with minimal trauma to the luminal tissue, for example, by providing a sutureless seal.

With regards to the arterial wall morphology, in the context of example embodiments directed to closing arterial perforations, the fibrous adventitial layer of an artery (i.e., the outer layer) is relatively tough, whilst the intimal and endothelial layers are friable. Because of the morphology of the arterial wall, an arteriotomy may be circumferential in nature and perpendicular to the longitudinal axis of the artery.

EXEMPLARY EMBODIMENTS

Figure 1:
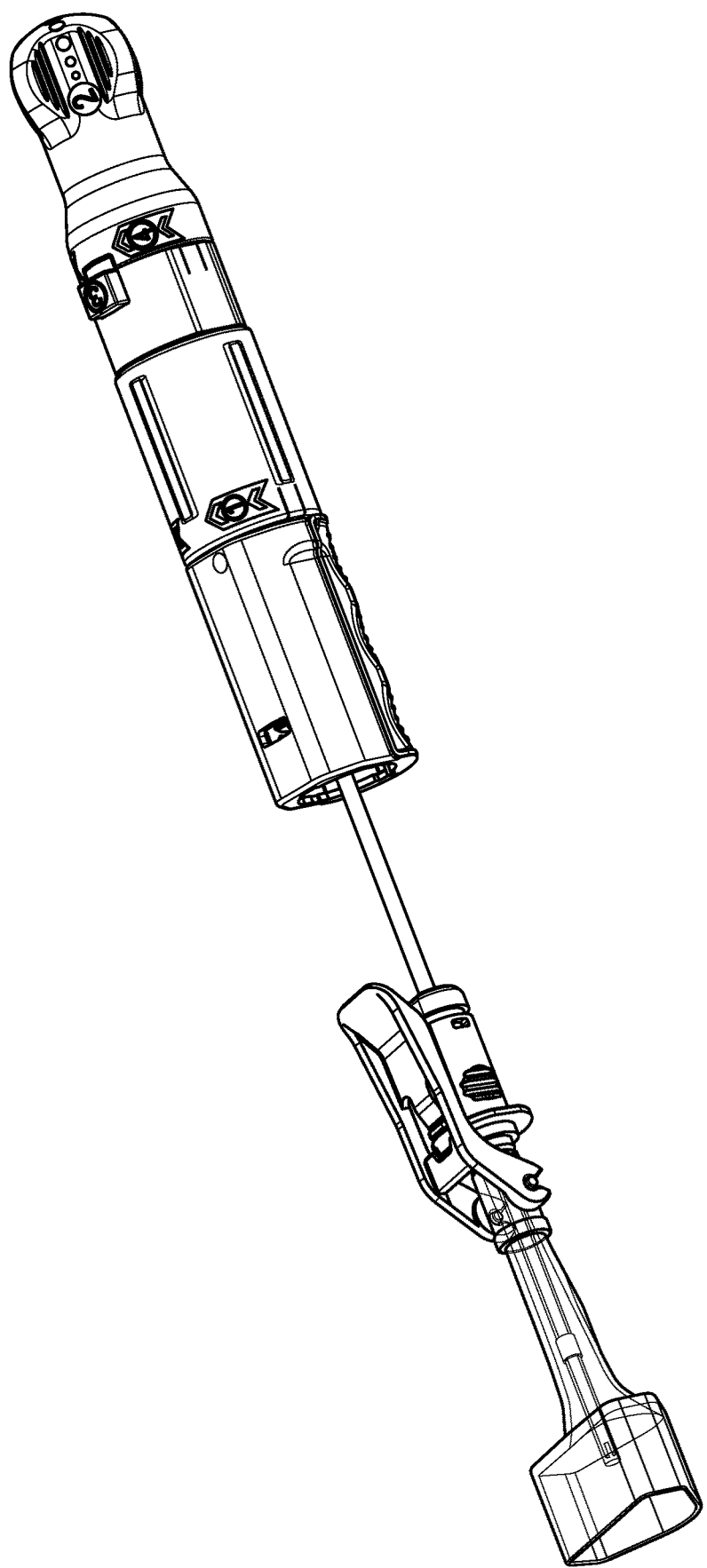
FIG. 1 depicts an image of an embodiment of an exemplary device as described herein in an unloaded state.
Figure 2A:
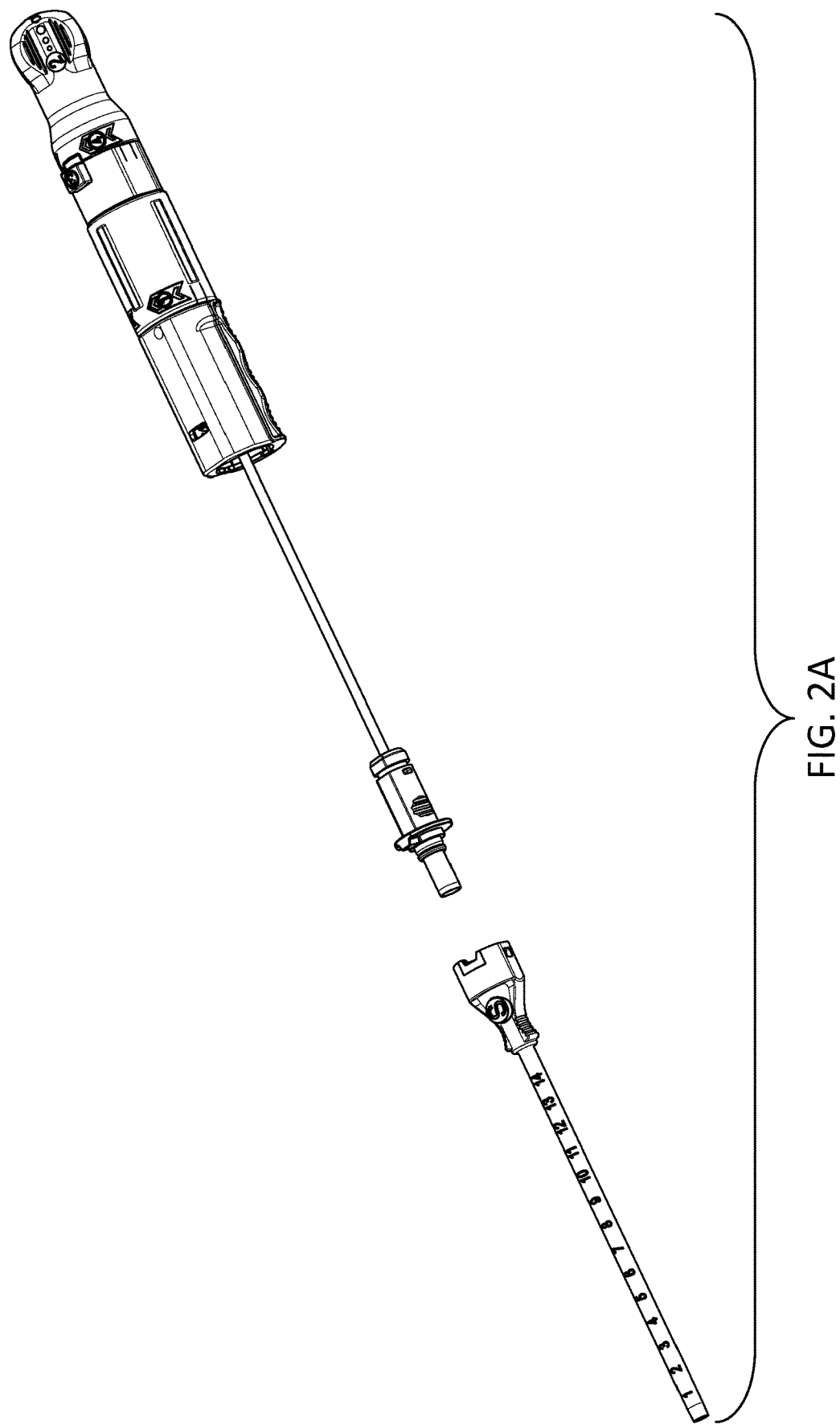
FIG. 2A depicts an image of an embodiment of a loaded device (advancement into introducer).
Figure 2B:
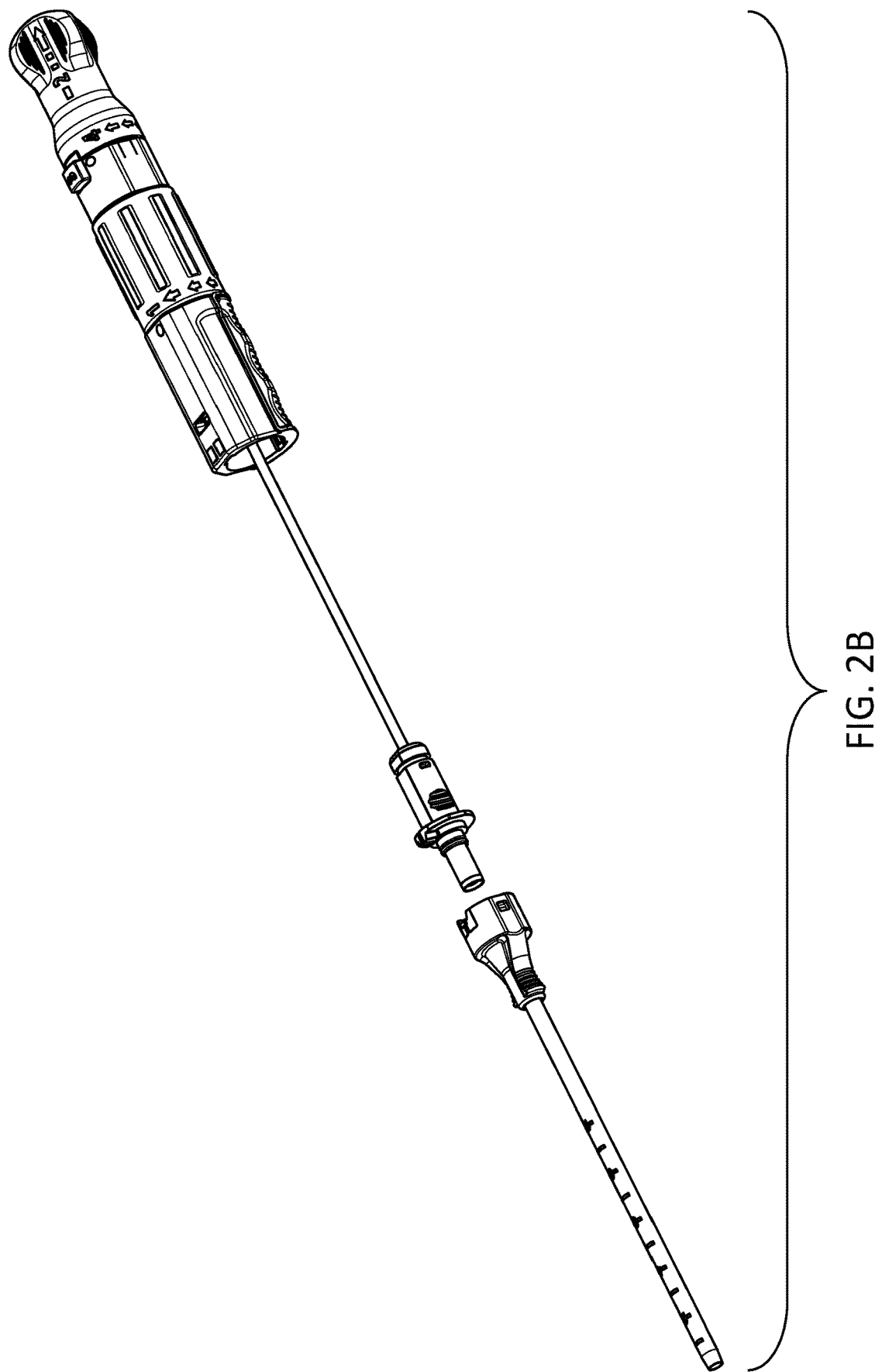
FIG. 2B depicts an image of an embodiment of a loaded device (advancement into introducer).

The methods and devices provided herein relate to devices that are capable of delivering an implant to close holes in hollow vessels. FIG. 1 depicts a pictorial image of an embodiment of the device in an unloaded state. FIGS. 2A and 2B depict images of certain embodiments of a device with the implant loaded, during advancement into an introducer.

In a certain embodiment, the device comprises the parts listed in Table 1 below; the functionality of each part is described in further detail below.

TABLE 1

| Part Name | Detail |
| --- | --- |
| Introducer unit | Sheath and Dilator |
| Sheath | Sheath shaft, sheath hub, haemostasis valve and sheath retainer |
| Dilator | Dilator shaft and dilator hub |
| Loading Funnel | Protects implant in packaging and facilitates implant loading |
| Lever | Maintains attachment of loading funnel to loading cannula |
| Cannula | Cannula tube, cannula seal, cannula cap and cannula retainer |
| Cannula tube | Protects the implant during insertion through the sheath seal |
| Cannula seal | Seal in the cannula cap |
| Cannula retainer | Locks cannula tube and cannula seal inside the cannula cap |
| Cannula cap | Houses the cannula tube and cannula seal |
| Sheath carriage | Connects to cannula |
| Handle front L | Operator grip area of the device |
| Handle front R | Operator grip area of the device |
| Handle centre | Joins front and back of the device |
| Sheath cam L | Actuates sheath carriage |
| Sheath cam R | Connected to sheath cam L |
| Handle end L | Houses hubs |
| Handle end R | Houses hubs |
| Cam lock | Locks back cam |
| Back cam L | Actuates release sleeve 86 and push tube hubs |
| Back cam R | Allows re-setting of the device |

TABLE 1-continued

| Part Name | Detail |
|---|---|
| Shafts | Release sleeve 86, retainer sleeve 84 & push tube 155 |
| Release sleeve 86 | Releases implant from the retainer sleeve 84 |
| Release sleeve hub | Moves release sleeve 86 |
| Retainer sleeve 84 | Holds implant in position |
| Retainer sleeve hub | Holds retainer tube |
| Push tube 155 | Tube to push the extra-arterial pin |
| Push tube hub | Moves push tube 155 |

Implant Loading

Figure 3:
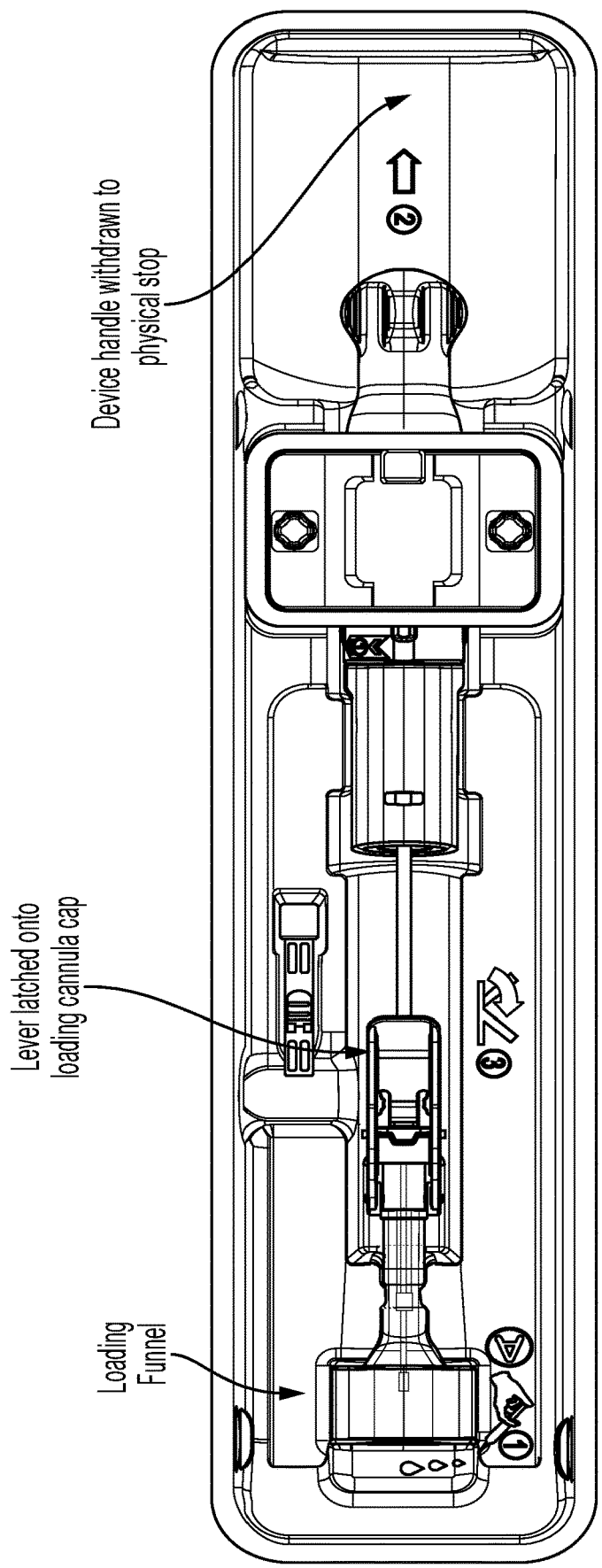
FIG. 3 depicts an image of an embodiment of a device in a packaging tray.
Figure 4C:
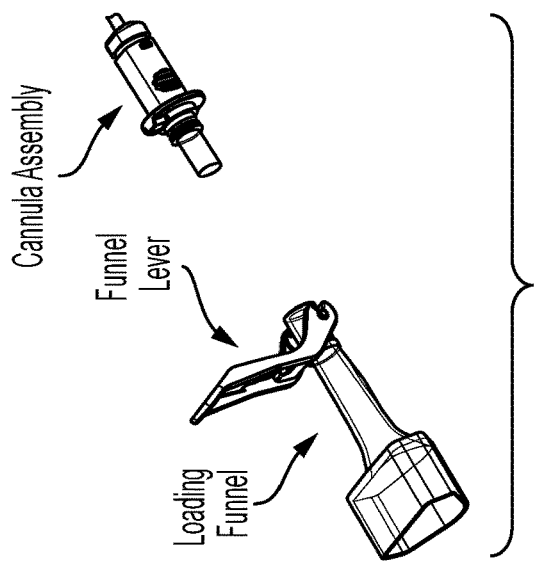
FIG. 4C depicts an image of an embodiment of a funnel-loading cannula cap arrangement with the funnel withdrawn from the loading cannula cap.
Figure 4B:
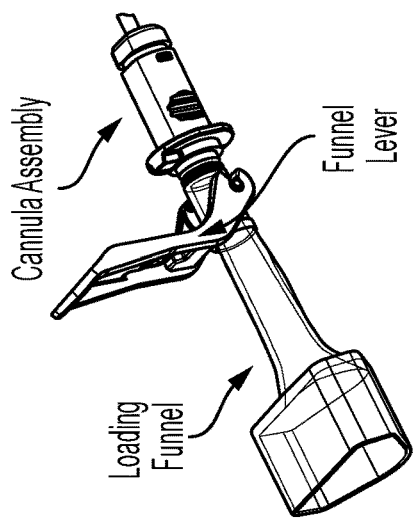
FIG. 4B depicts an image of an embodiment of a funnel-loading cannula cap arrangement with a lever detached from the loading cannula cap.
Figure 4A:
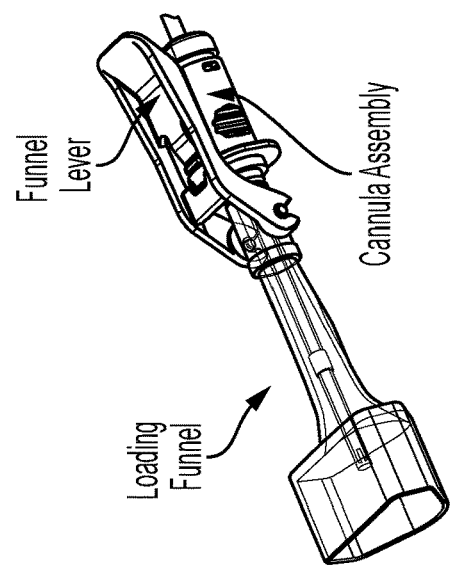
FIG. 4A depicts an image of an embodiment of a funnel-loading cannula cap arrangement with a lever latched onto the loading cannula cap.
Figure 5B:
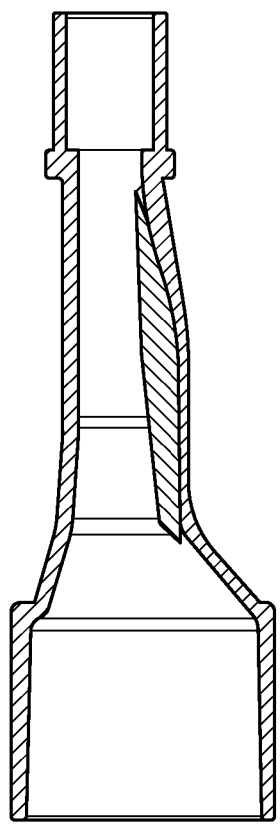
FIG. 5B depicts an image of an isometric view of a loading funnel.
Figure 5A:
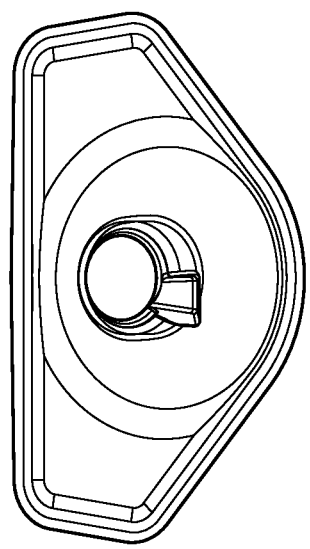
FIG. 5A depicts an image of the front view of a loading funnel with an internal design to accommodate loading of the implant.
Figure 6A:
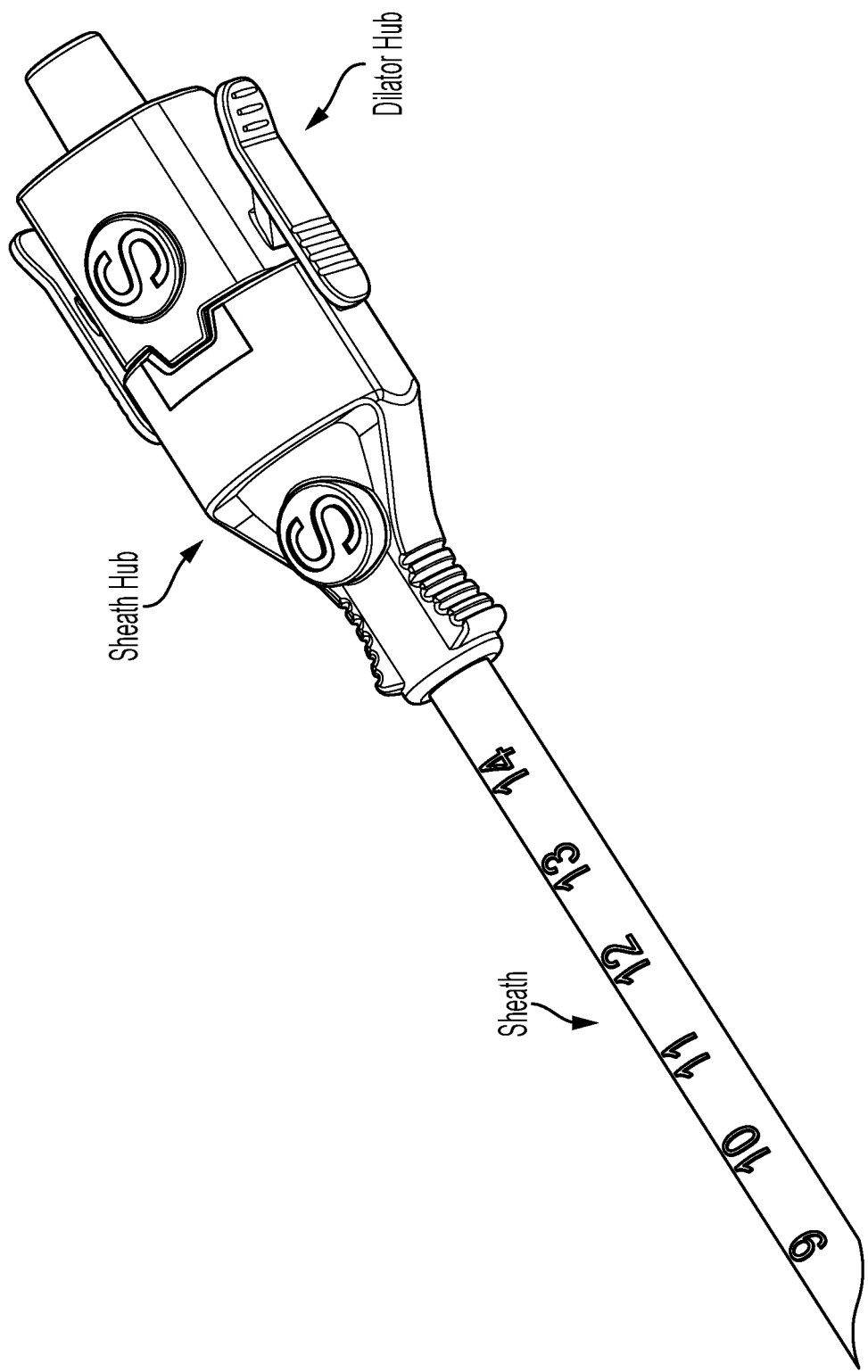
FIG. 6A depicts an image of an exemplary embodiment of a sheath and dilator introducer unit.
Figure 6B:
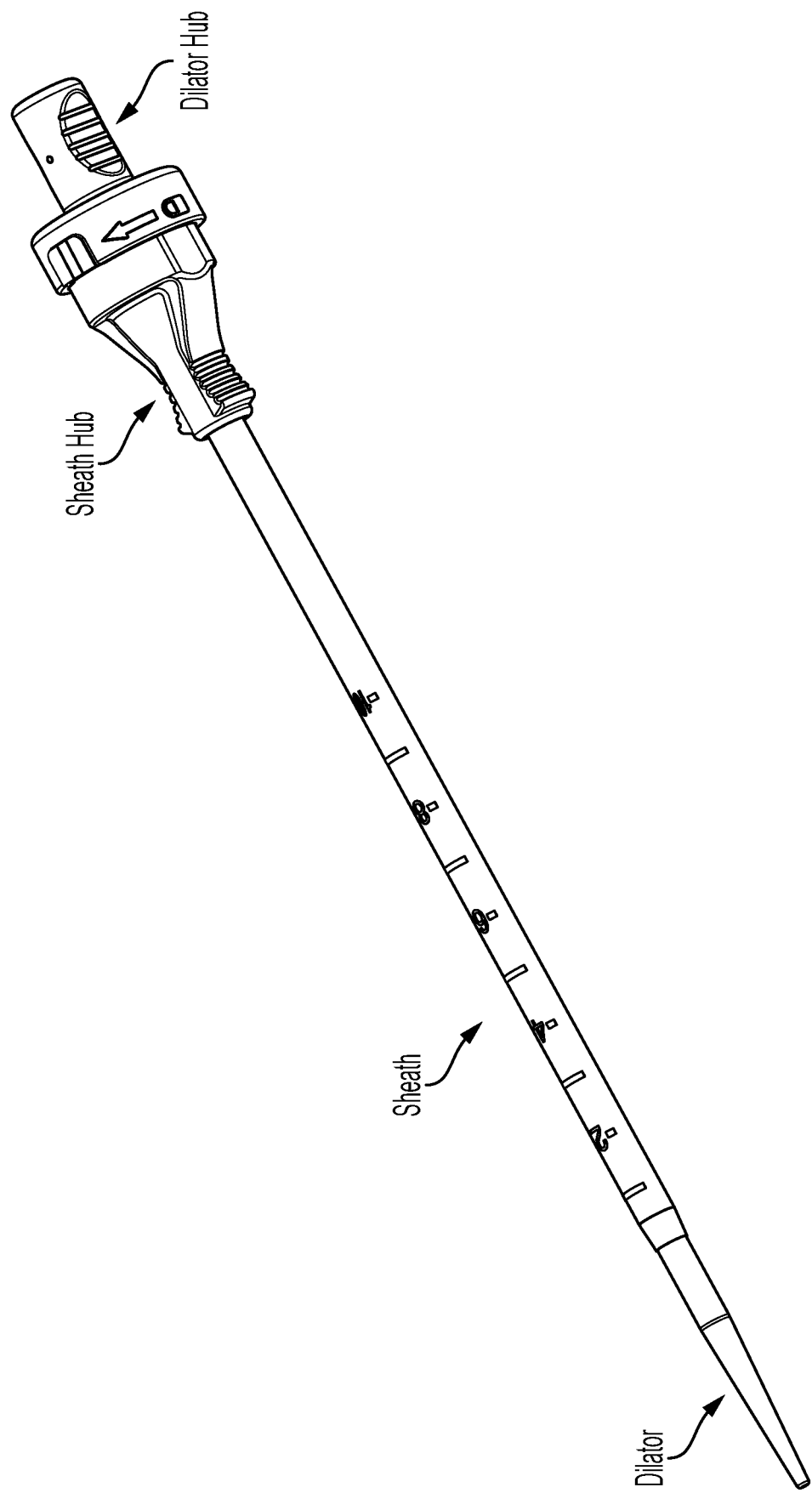
FIG. 6B depicts an image of an exemplary embodiment of a sheath and dilator introducer unit.
Figure 7B:
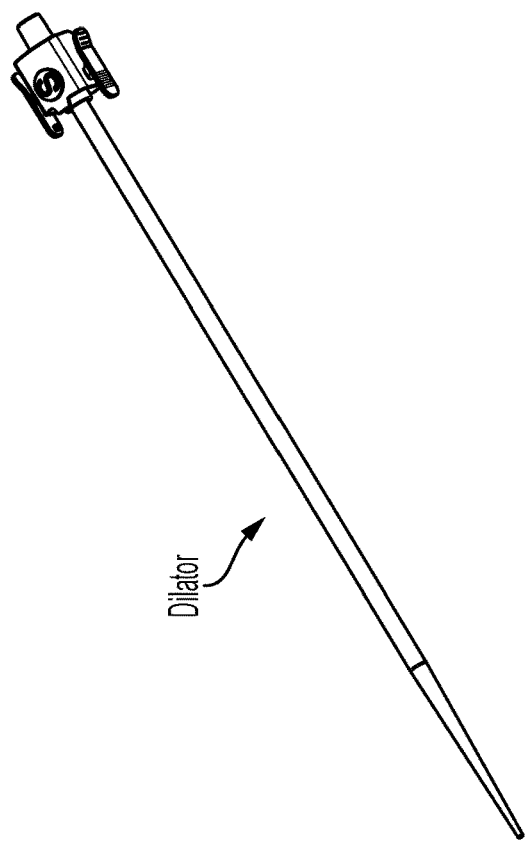
FIG. 7B depicts an image of an embodiment of a dilator.
Figure 7A:
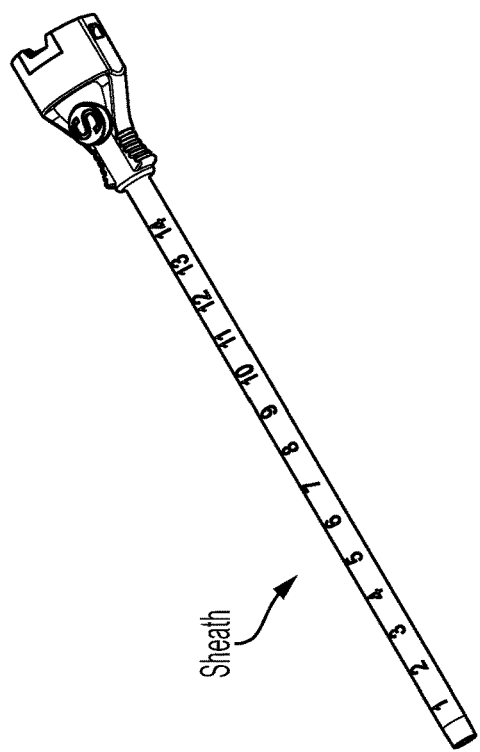
FIG. 7A depicts an image of an embodiment of an introducer sheath.
Figure 7D:
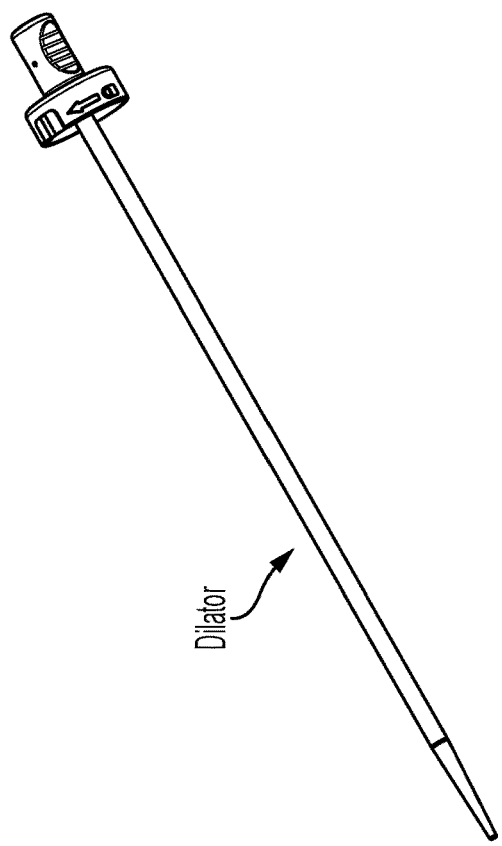
FIG. 7D depicts an image of an embodiment of a dilator.
Figure 7C:
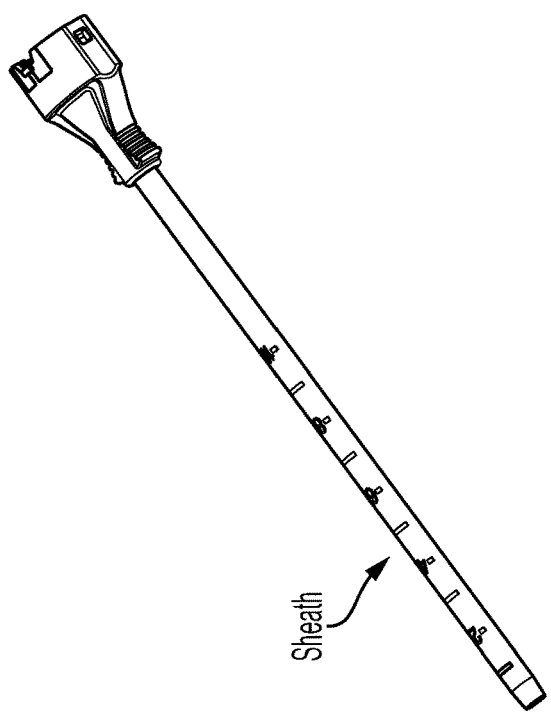
FIG. 7C depicts an image of an embodiment of an introducer sheath.

In certain embodiments, a delivery system, e.g., as described herein, is packaged in a tray system, e.g., with the implant located in the loading funnel. In certain embodiments, to load the implant, the device is held by the back handle section and pulled to a physical and tactile feel stop in the tray (see, e.g., FIG. 3). In certain embodiments, at this stage, the implant is loaded into a (loading) cannula assembly (the cannula assembly and its components are described below). A funnel lever is then unlatched from the (loading) cannula cap, and the device is withdrawn from the tray in a backward motion leaving the funnel and lever in the tray (see FIGS. 4A-C). In certain embodiments, the loading funnel is designed so as to ensure that the implant is folded concentrically (e.g., in an overlapping manner) as the implant is withdrawn backward into and/or through the funnel and loaded into the cannula (see, e.g., FIGS. 5A-B).

Introducer Unit

The introducer unit comprises a sheath and dilator (see, e.g., FIGS. 6A and 6B, and FIGS. 7A-7D), and may have shafts of varying lengths, diameters, and/or French sizes. In certain embodiments, the introducer unit comprises a graduated scale on the sheath shaft (or sheath outer shaft) and a blood signal in the dilator shaft. In certain embodiments, when used in combination, these provide the operator with visual indicators of relative location of the introducer and the device delivery system during initial deployment of the sheath to the, e.g., arteriotomy, and again during the deployment of the implant. In certain embodiments, the graduated scale on the sheath shaft and the blood signal, used in combination, allow the operator to identify the position of the implant during deployment, and to deploy the implant in the correct or desired location. In certain embodiments, the dilator loads onto and/or travels over a guide wire (e.g., a 0.035" guide wire), which occupies the internal diameter of the dilator at the distal tip and proximal hub areas. In certain embodiments, the dilator contains a blood signaling hole in the hub which is fed from a blood signal hole located in close proximity (e.g., just distal) to the sheath tip, e.g., on the tapered portion of the dilator.

In certain embodiments, when the introducer unit (e.g., sheath and dilator) enters the, e.g., arteriotomy, (e.g., when the introducer is moved along the wire and the tip of the dilator enters an arteriotomy) blood enters the dilator at the blood signal hole (e.g., as soon as the blood signal hole on the distal tip of the dilator enters a blood vessel), and travels up the dilator's lumen, and exits the dilator at a signal hole (e.g., a blood signal detector hole) on the dilator hub. This signals to the operator that the sheath tip is just about to enter the, e.g., arteriotomy. The graduations on the sheath shaft can then provide to the operator an indication of the tissue tract depth, as this point on the graduated scale (at the skin level) indicates the depth of the tissue tract (mark X). From this point on the graduated scale (mark X), the introducer unit is advanced by a certain distance (4 cm) into the vessel to mark Y (going by the graduated scale on the sheath). The dilator is subsequently removed from the sheath, while maintaining the sheath at the 'Y' location in the vessel, and keeping the guidewire in its relative position.

Sheath Hub and Dilator

Figure 8A:
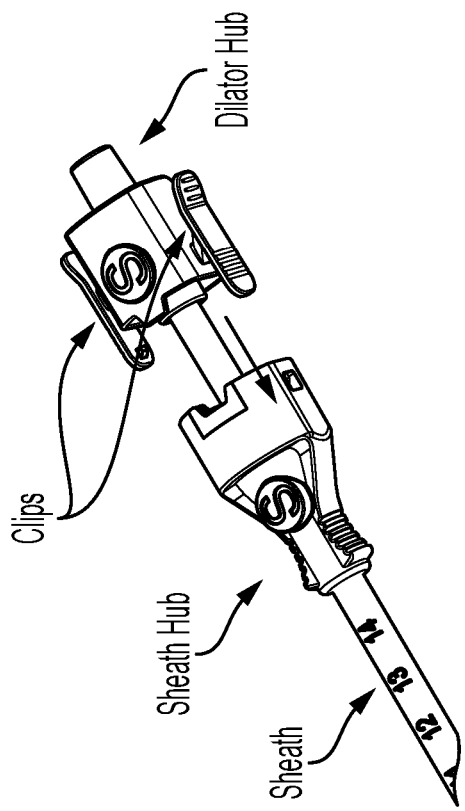
FIG. 8A depicts an image of a sheath hub and dilator hub connection, particularly the insertion of a dilator into an introducer sheath.
Figure 8C:
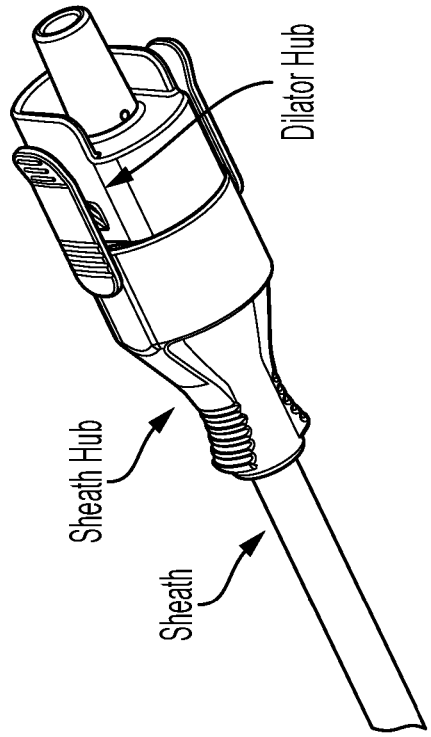
FIG. 8C depicts an image of a sheath hub and dilator hub connection, with the dilator fully inserted into an introducer sheath and with the dilator hub locked in the sheath hub.
Figure 8B:
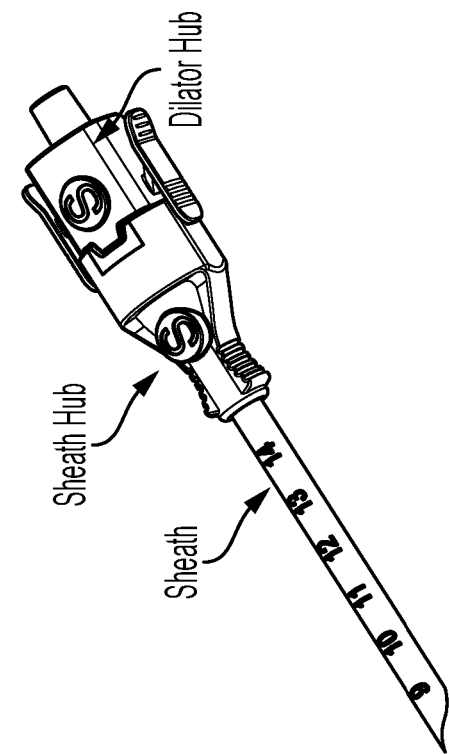
FIG. 8B depicts an image of a sheath hub and dilator hub connection with the dilator fully inserted into an introducer sheath.
Figure 8D:
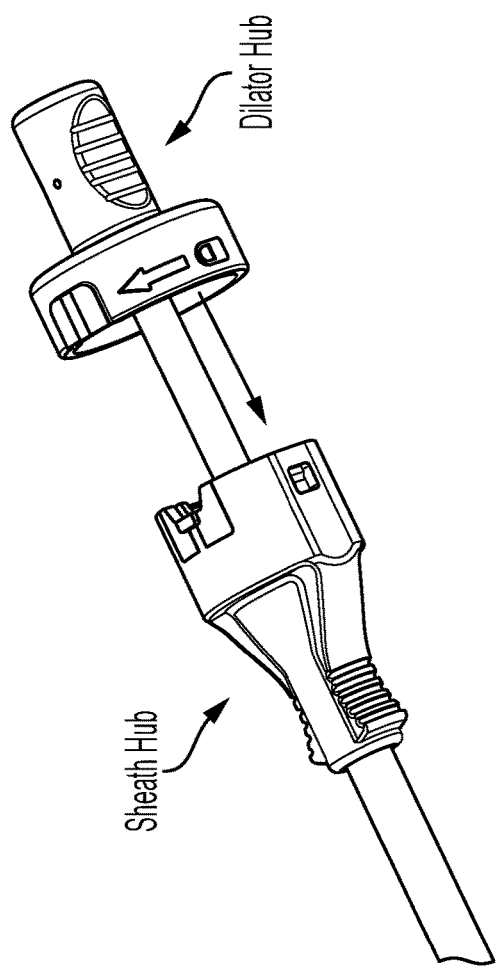
FIG. 8D depicts an image of a sheath hub and dilator hub connection, particularly the insertion of a dilator into an introducer sheath.
Figure 8F:
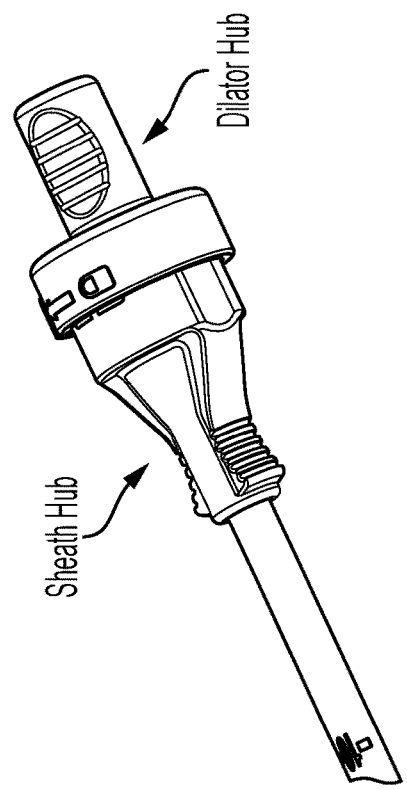
FIG. 8F depicts an image of a sheath hub and dilator hub connection, with the dilator fully inserted into an introducer sheath and with the dilator hub locked in the sheath hub.
Figure 8E:
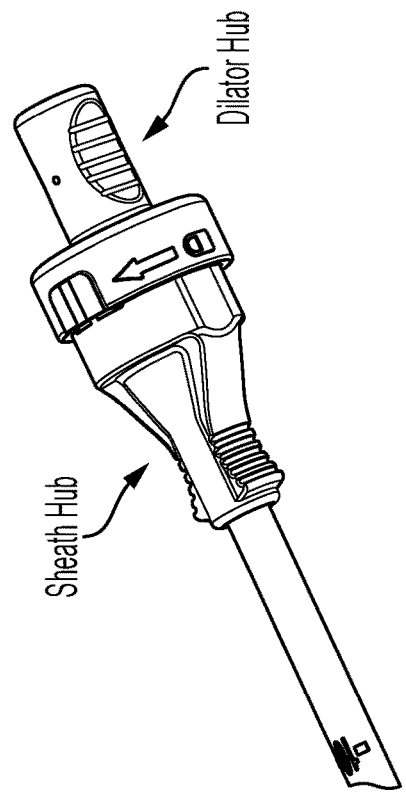
FIG. 8E depicts an image of a sheath hub and dilator hub connection with the dilator fully inserted into an introducer sheath.
Figure 9A:
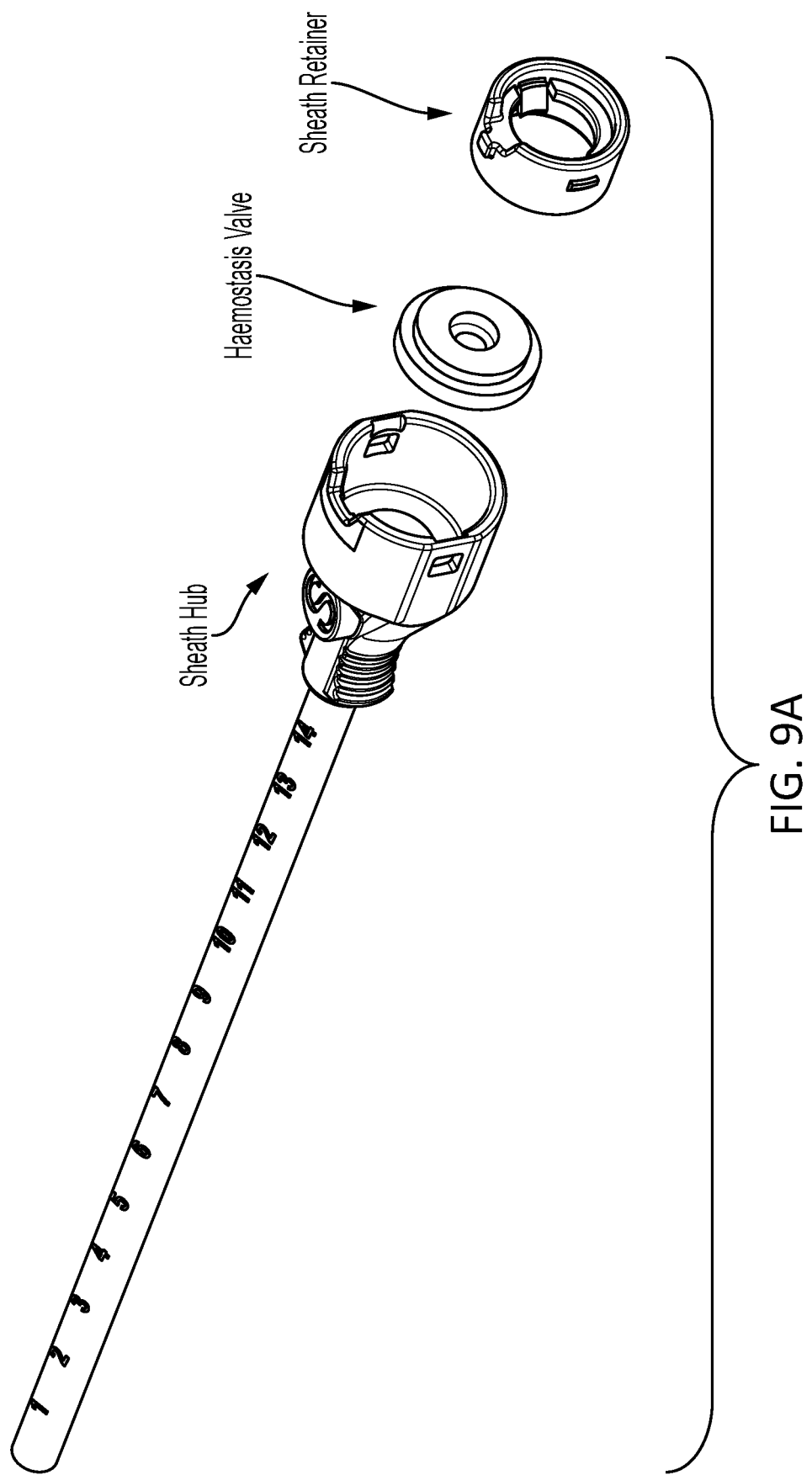
FIG. 9A depicts an image of an exploded view of a sheath assembly including a sheath hub, a haemostasis valve, and a sheath retainer.
Figure 9B:
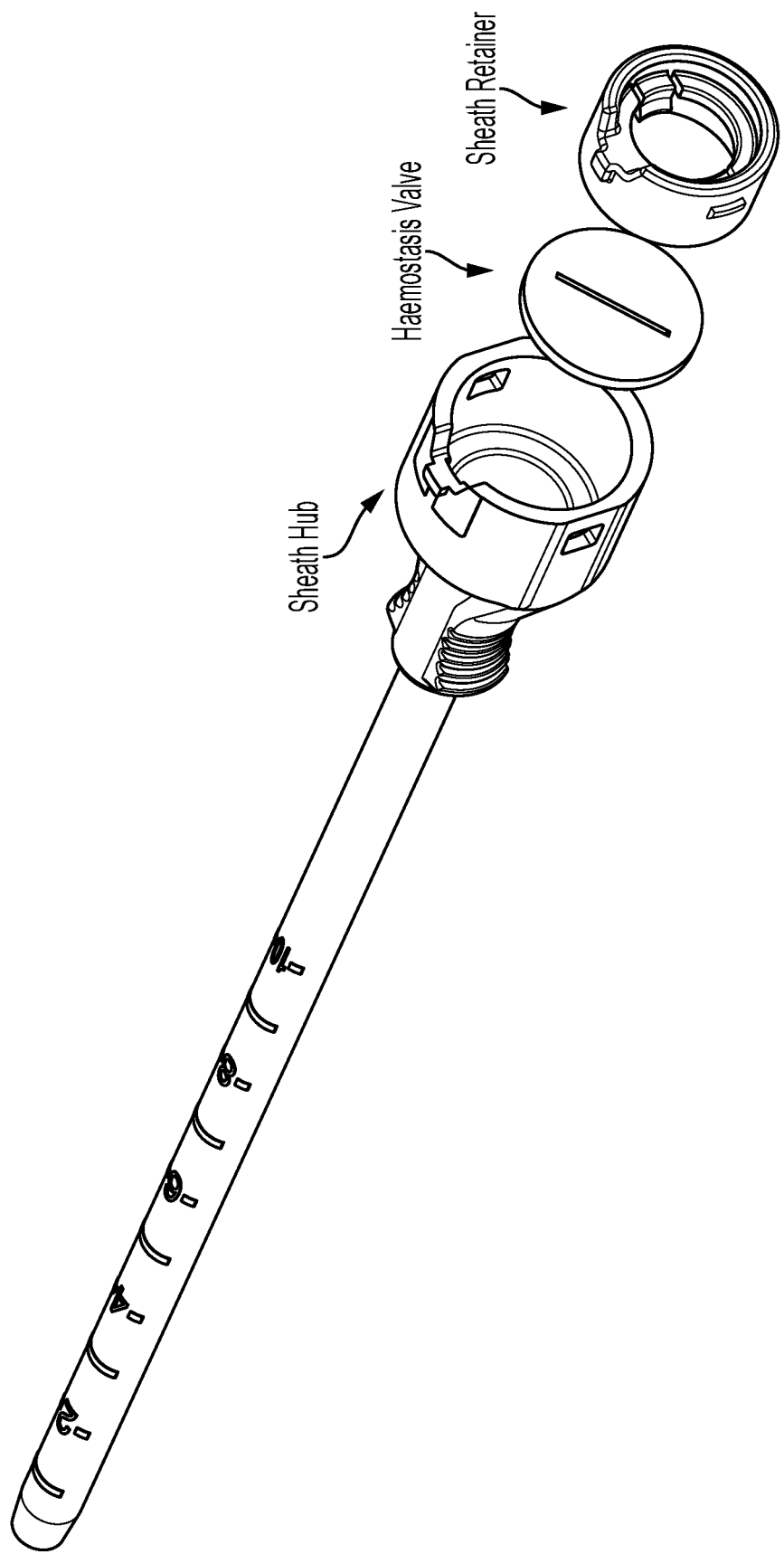
FIG. 9B depicts an image of an exploded view of a sheath assembly including a sheath hub, a haemostasis valve, and a sheath retainer.
Figure 10B:
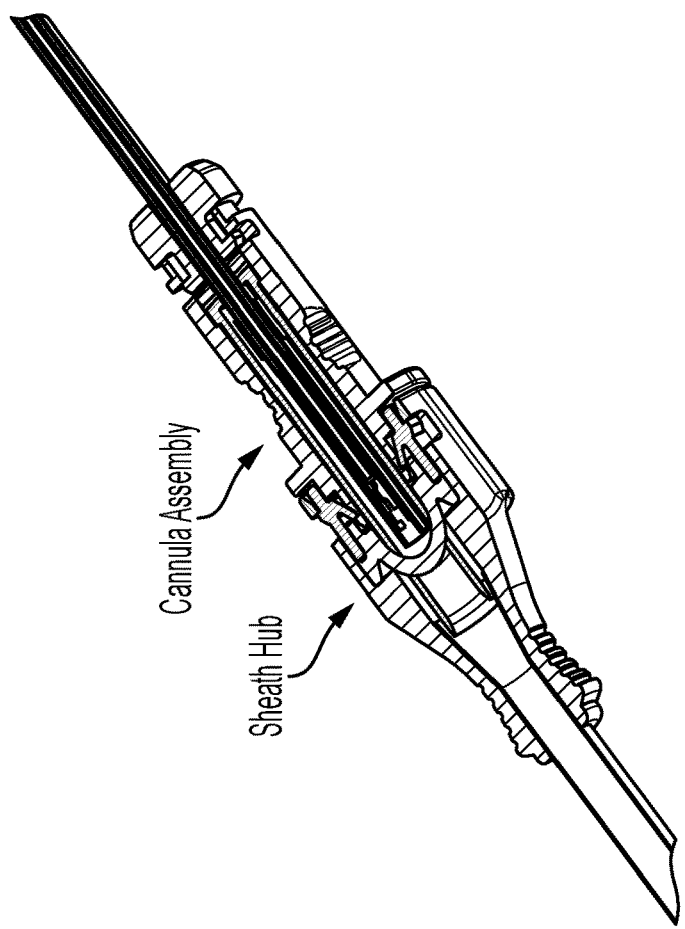
FIG. 10B depicts an image of a sheath hub connected to a cannula cap (cross-sectional view).
Figure 10A:
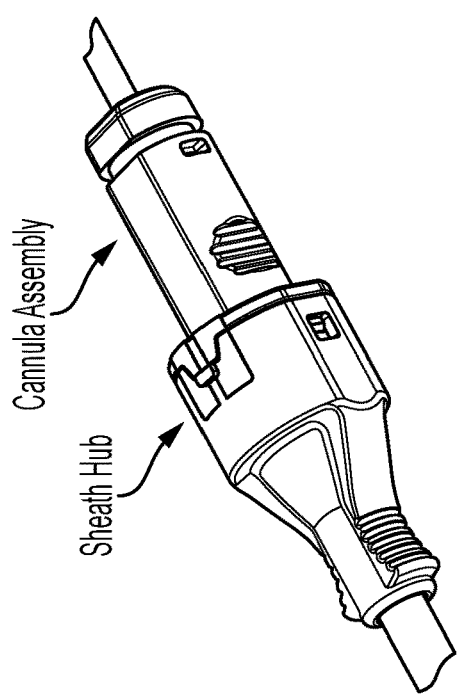
FIG. 10A depicts an image of a sheath hub connected to a cannula cap (external view).
Figure 10D:
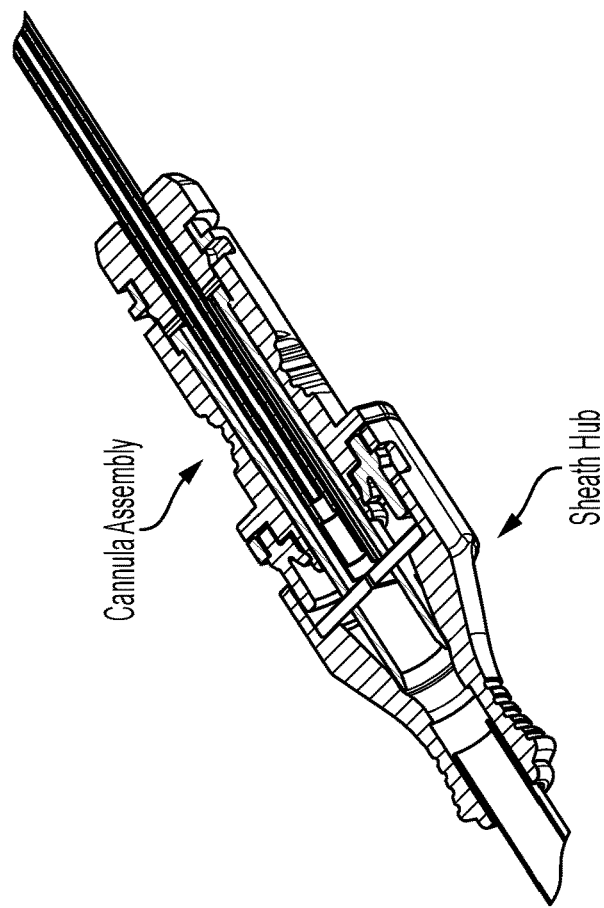
FIG. 10D depicts an image of a sheath hub connected to a cannula cap (cross-sectional view).
Figure 10C:
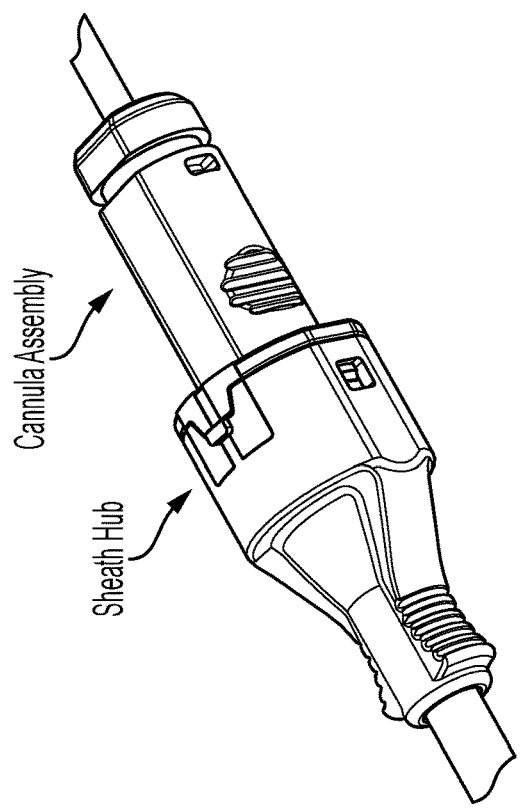
FIG. 10C depicts an image of a sheath hub connected to a cannula cap (external view).
Figure 11B:
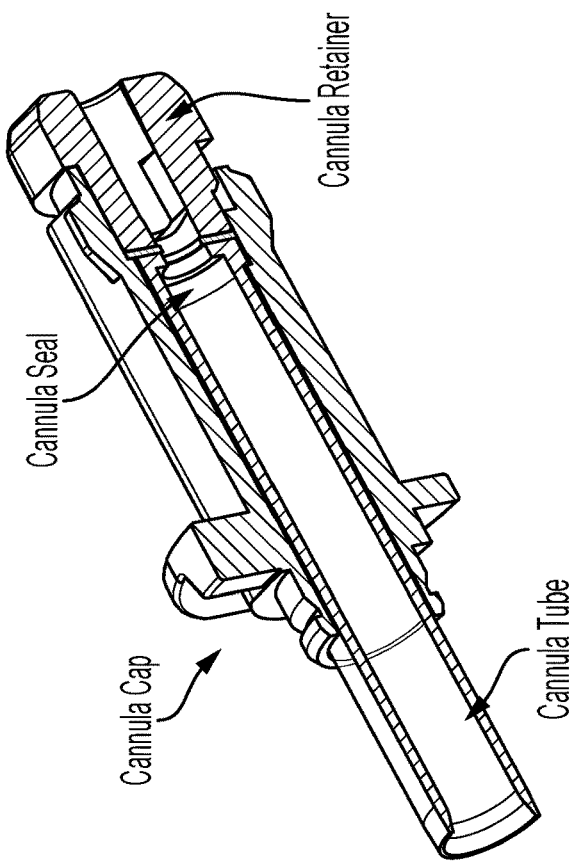
FIG. 11B depicts an image of a cannula (cross-sectional view).
Figure 11A:
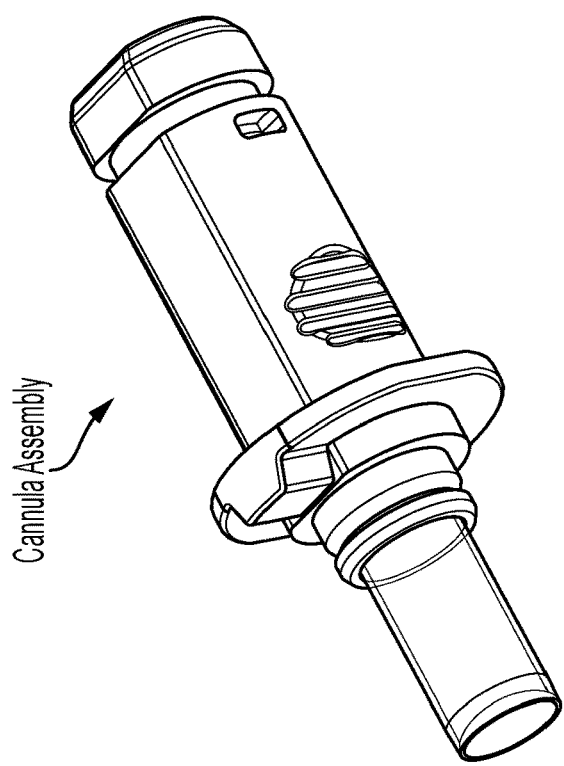
FIG. 11A depicts an image of a cannula (external view).
Figure 11D:
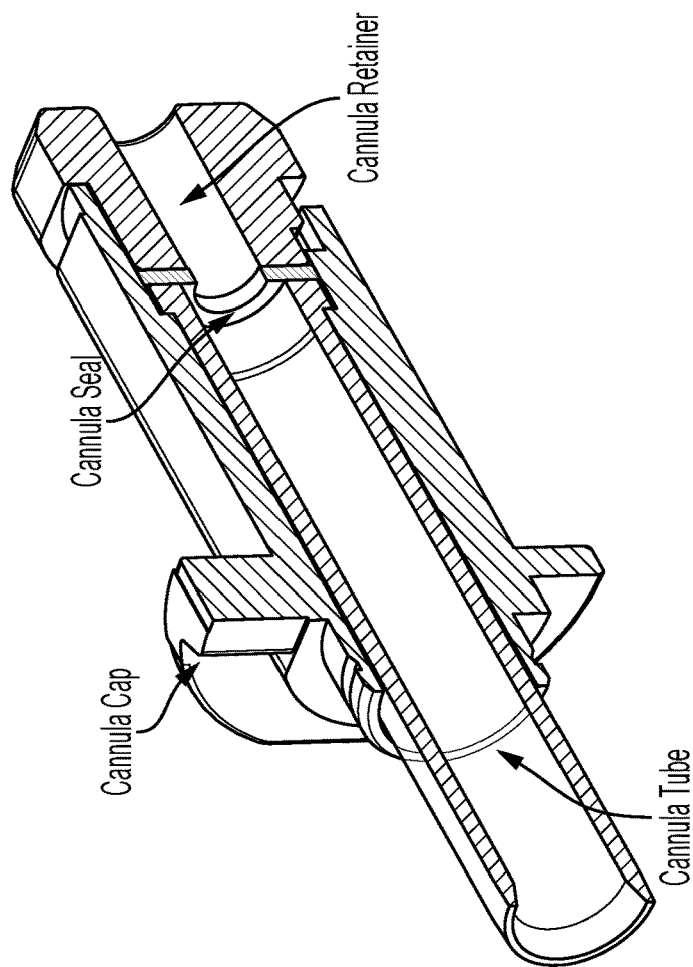
FIG. 11D depicts an image of a cannula (cross-sectional view).
Figure 11C:
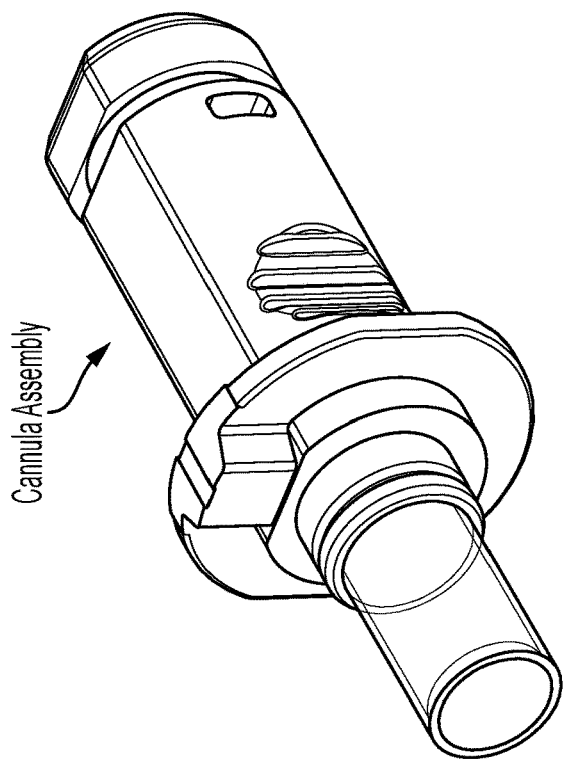
FIG. 11C depicts an image of a cannula (external view).

In certain embodiments, the sheath hub is designed to connect with the dilator hub using, e.g., a spring clip mechanism (see, e.g., FIGS. 8A-8C) or a bayonet mechanism (see, e.g., FIGS. 8D-8F), wherein the dilator hub is pushed into the sheath hub and, e.g., engaged (e.g., clicked) and/or twisted to lock in position (FIG. 8F). In certain embodiments, e.g., in embodiments comprising a spring clip mechanism, tabs on the distal end of a spring clip mechanism latch onto, e.g., pockets on the sheath hub, holding both hubs firmly together. In certain embodiments, to separate the hubs, one or more proximal end or ends of a clip or clips is/are compressed, causing on or more tabs to exit their corresponding pocket on the sheath hub, allowing the dilator to be withdrawn from the sheath (see, e.g., FIGS. 8A-8C). In certain embodiments, the sheath hub is also designed to connect with the cannula. In certain embodiments, the haemostasis valve is secured into the sheath hub by the sheath retainer (see, e.g., FIGS. 9A and 9B). In certain embodiments, the sheath retainer has snap features which align with snap features on the cannula cap to facilitate connection and locking into position (see, e.g., FIGS. 10A-10D).

Cannula

Figure 12A:
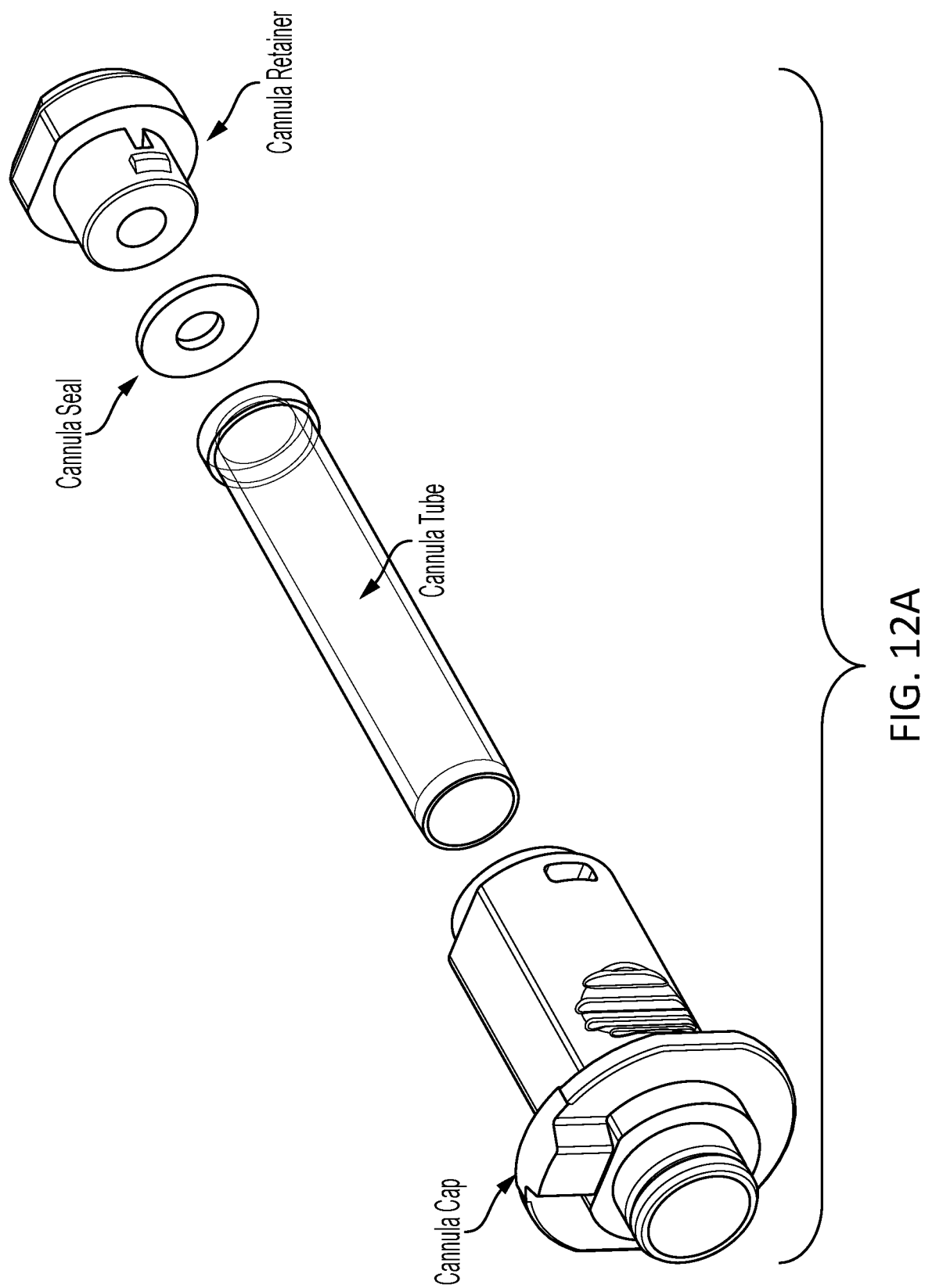
FIG. 12A depicts an image of an exploded view of a cannula assembly including a cannula cap, a tube, a seal, and a retainer.

In certain embodiments, the cannula or cannula assembly includes a cannula cap, cannula tube, cannula seal, and cannula retainer (see FIGS. 11A-11D). The components can be seen, e.g., in FIGS. 12A and 12B. In certain embodiments, the cannula is part of the distal tip of the delivery device. In certain embodiments, the cannula is not part of the distal tip of the delivery device. In certain embodiments, the implant is loaded into the cannula from its resting position in the device tray packaging. In certain embodiments, during the first steps of implant deployment, the cannula is connected to the hub of the introducer sheath. Next, the delivery device is advanced towards the introducer sheath hub and the implant is delivered down to a position just proximal to the distal tip of the introducer sheath. The cannula engages and locks into the introducer sheath hub to form a single unit. In certain embodiments, the implant is loaded into the cannula, which is assembled onto a tip of a shaft of the device. When the cannula is connected to the sheath, the shafts of the device are advanced to push the implant out of the cannula to the end of the sheath. The (cannula) seal functions to stop the blood from flowing out the back of the cannula along the shaft during deployment of the device.

Sheath Withdrawal (Handle Front, Sheath Carriage, Cannula and Sheath)

Figure 13:
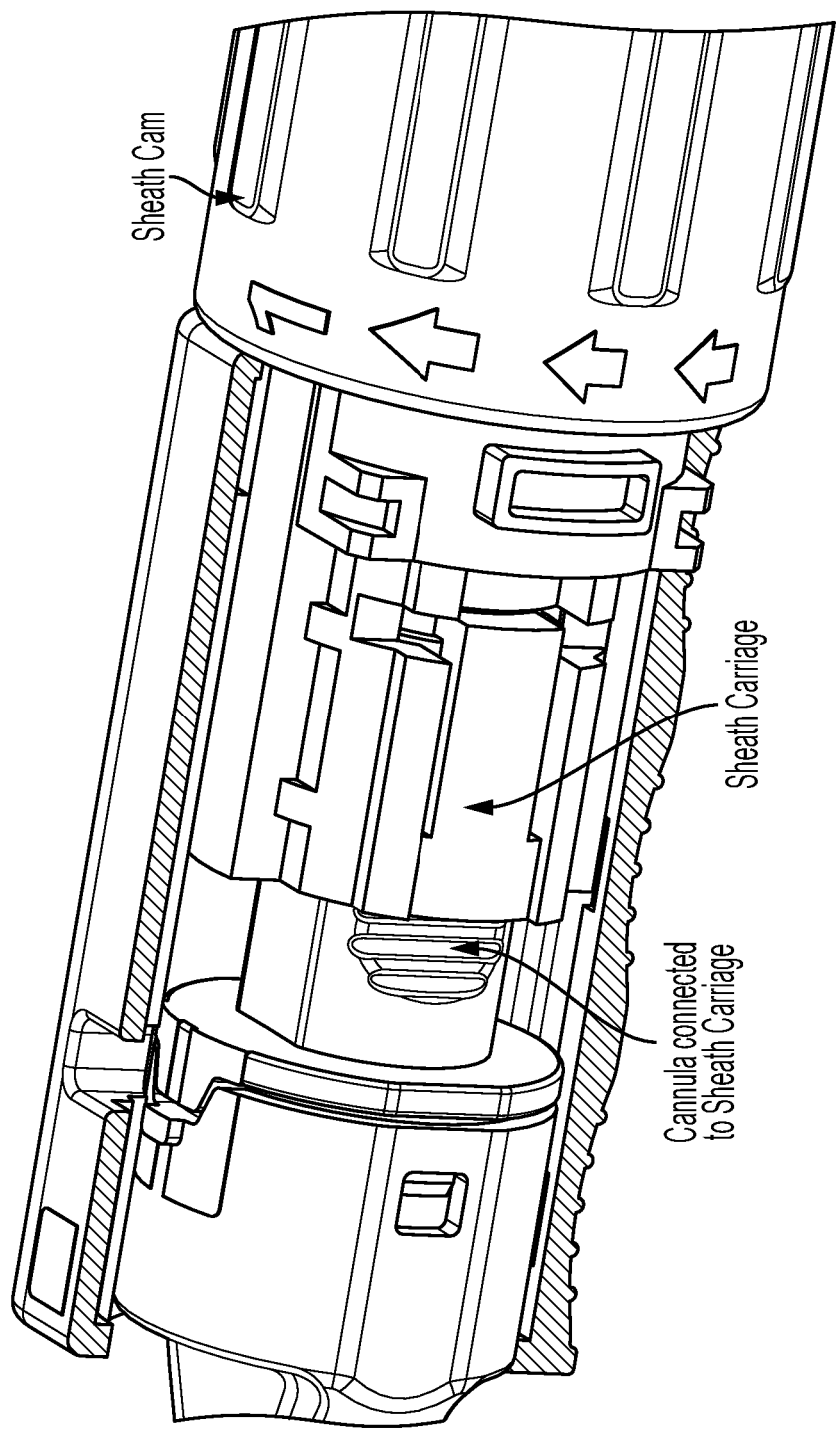
FIG. 13 depicts an image of a cannula and a sheath hub, wherein the cannula and sheath hub are connected into a sheath carriage.
Figure 14:
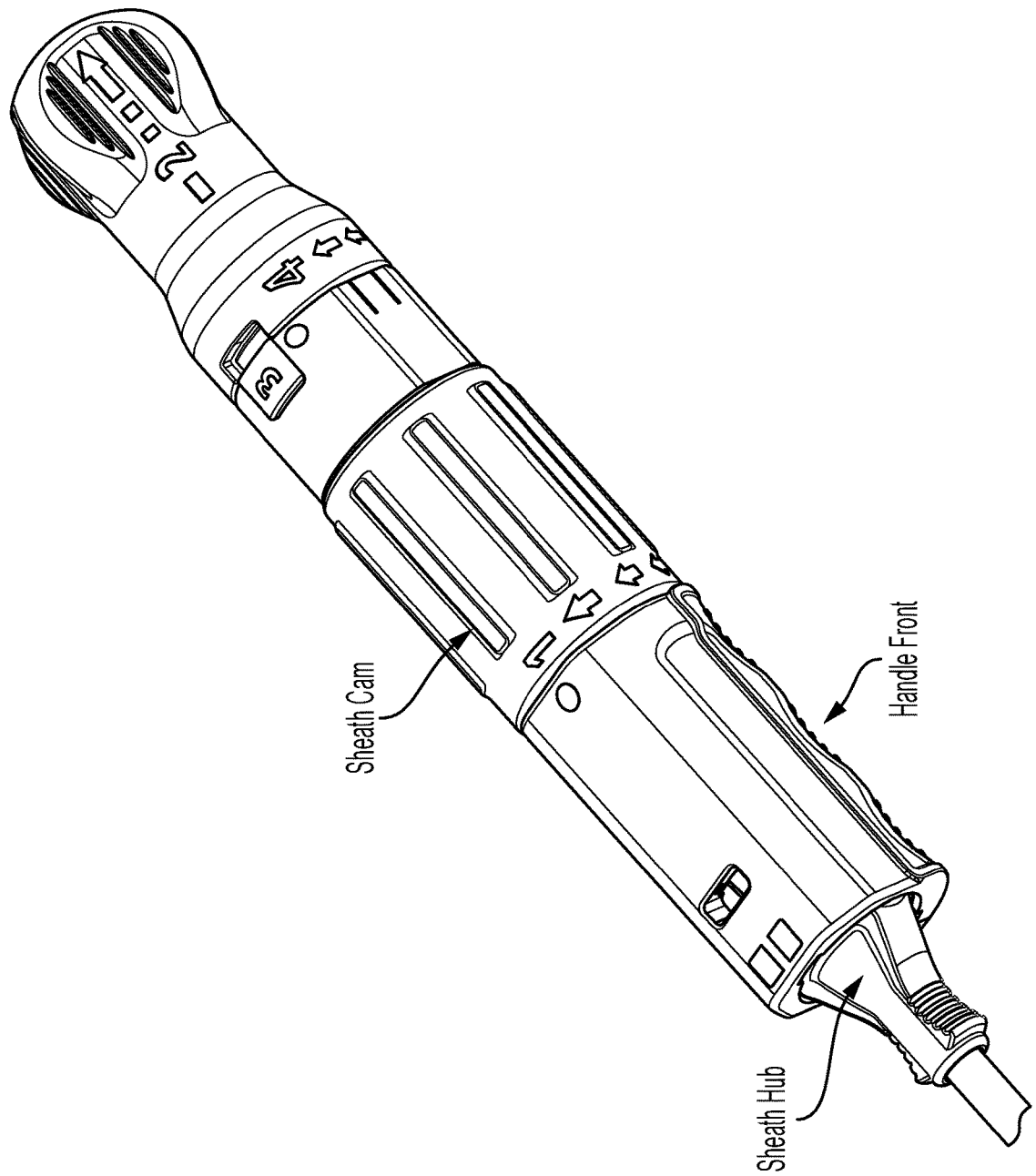
FIG. 14 depicts an image of a cannula and a sheath hub, wherein the cannula and sheath hub are connected into a sheath carriage inside the handle front.
Figure 15:
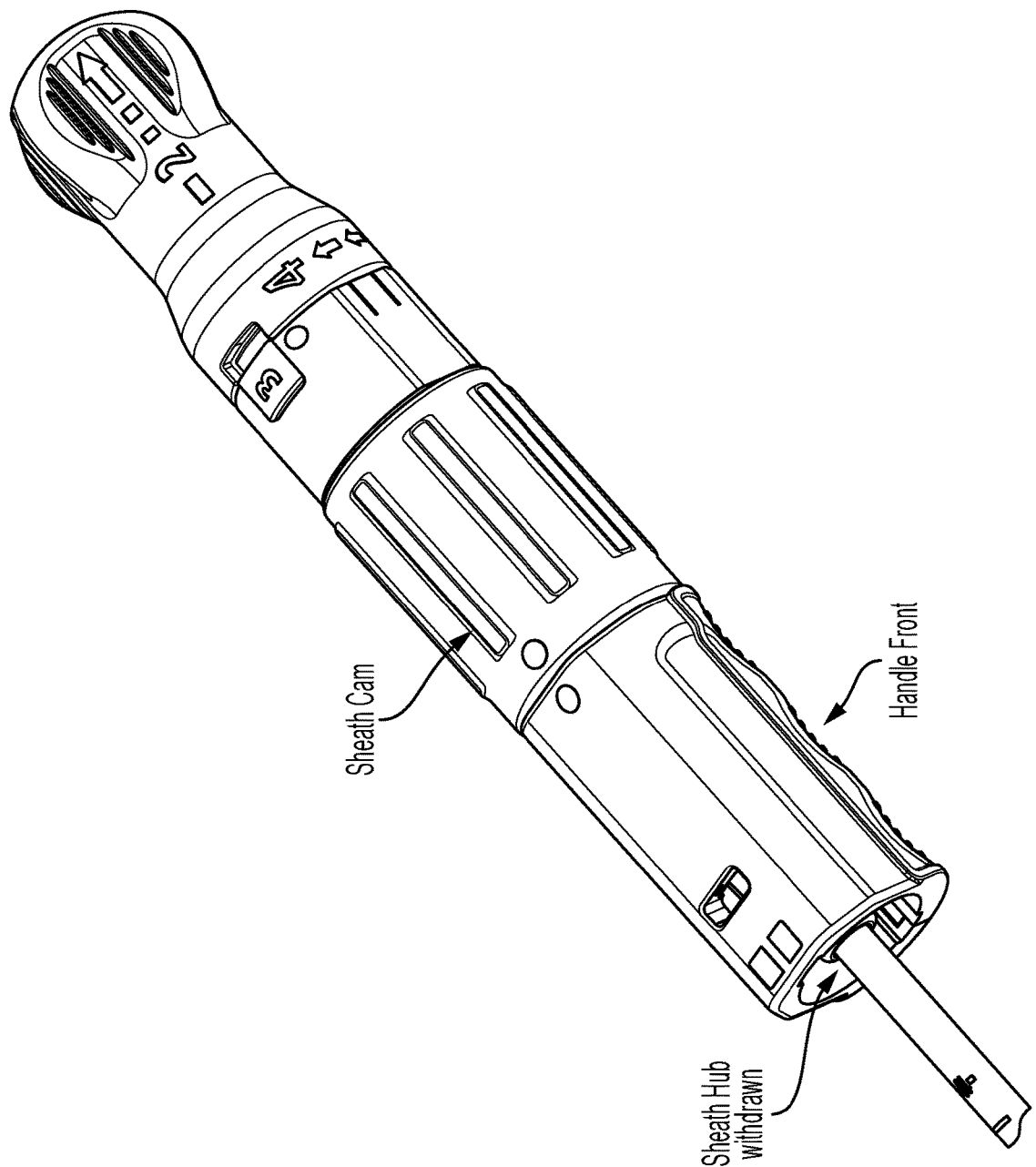
FIG. 15 depicts an image of a device assembly, wherein the sheath hub is withdrawn into the handle front.

In certain embodiments, the delivery handle is moved into close proximity to the introducer sheath hub. In certain embodiments, the cannula is designed to enter and lock and/or fit securely into the handle of the device. The cannula (connected to the sheath) is moved back and connected into the sheath carriage inside the handle front as shown in FIG. 13 and FIG. 14. In certain embodiments, a sheath cam is engaged with the sheath carriage and is then rotated from a first position (FIG. 14) to a second position, e.g., clockwise 180° which in turn actuates the sheath carriage and pulls back the sheath into the handle front (see FIG. 15). In certain embodiments, the result of this action is, for example, to expose the implant in the vessel in an atraumatic way by pulling the introducer sheath assembly in the proximal direction relative to the delivery handle. In certain embodiments, the user then (e.g., gradually) withdraws the device and sheath (assembly) (e.g., fully or partially) together from the artery (or other vessel, such as a vein), watching the graduations on the sheath until the mark X is reached. In certain embodiments, when the mark X on the graduated scale is reached, the user can feel the sheath tip exit the arteriotomy (or other vessel incision or access point) and within a certain distance (e.g., 1.5 cm) further withdrawal, can feel a back pressure as a result of the implant anchoring itself against the inside of, for example, a lumen of an artery wall (or other vessel, such as a vein) (this is the tamponade position).

Release of the Bioabsorbable Implant (Handle End, Cam Lock, and Back Cam)

Figure 16:
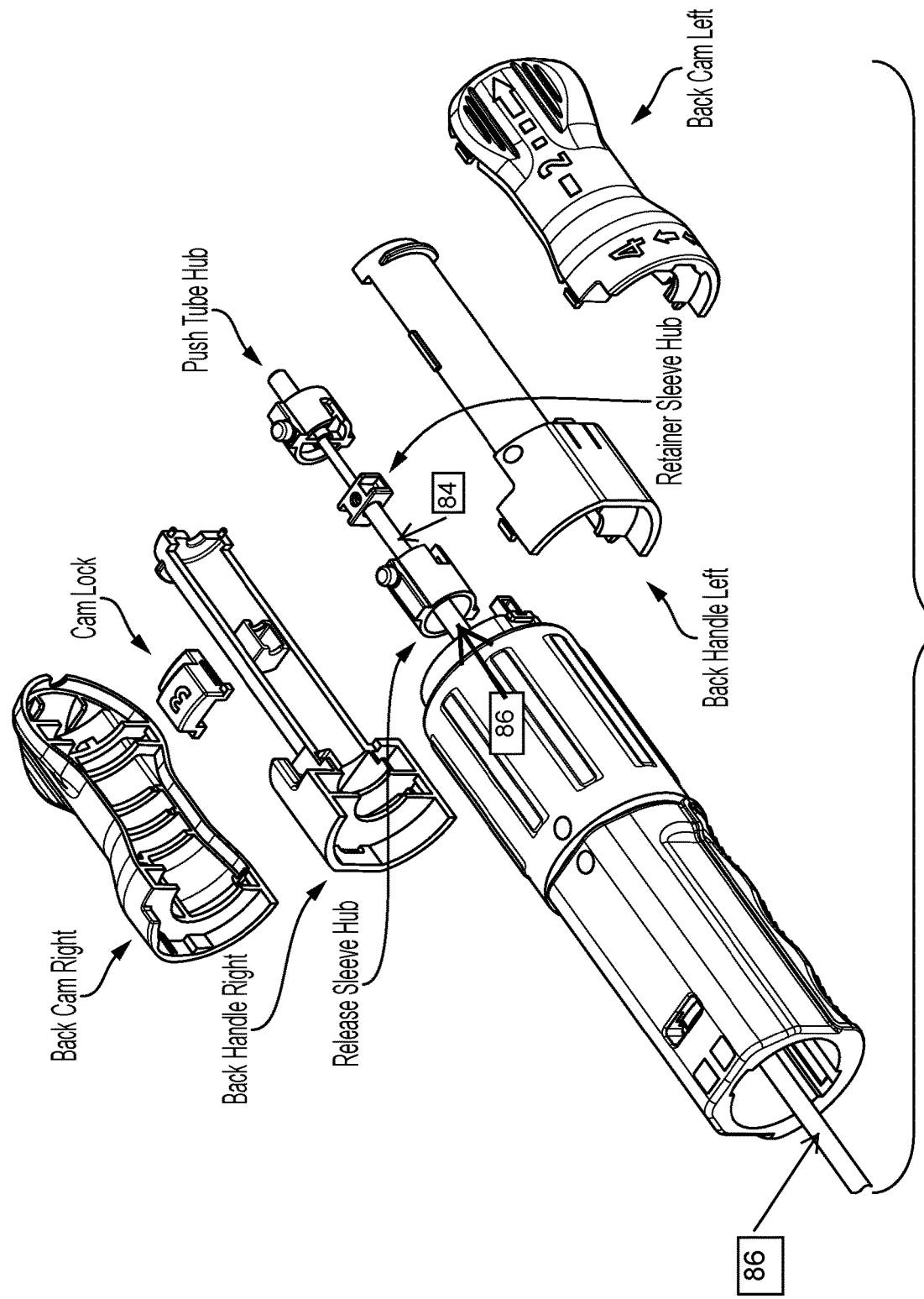
FIG. 16 depicts an image of an exploded view of shaft hubs, handle ends, a cam lock, and a back cam.
Figure 17:
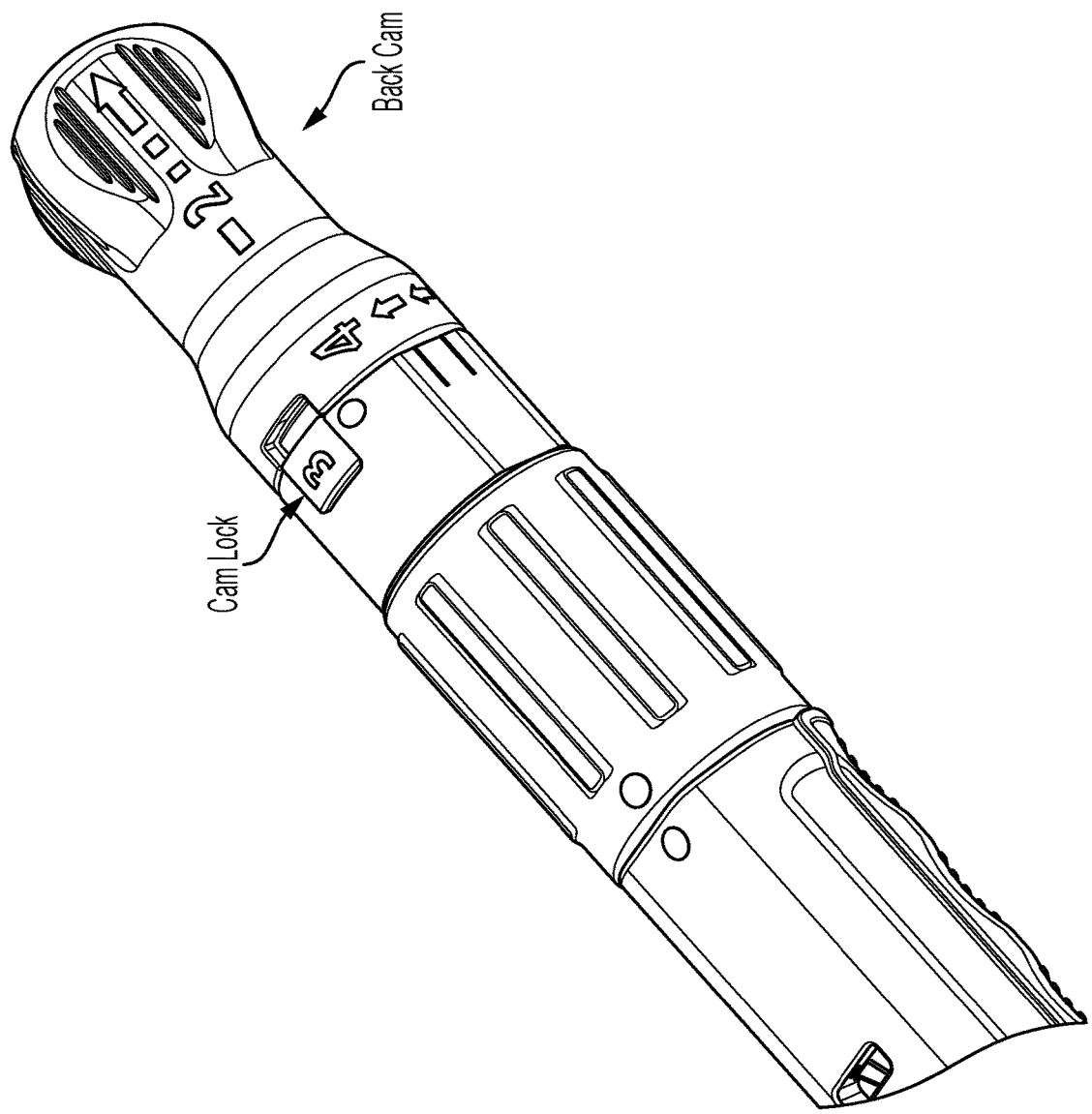
FIG. 17 depicts an image of a device assembly, wherein the cam lock is depressed.
Figure 18:
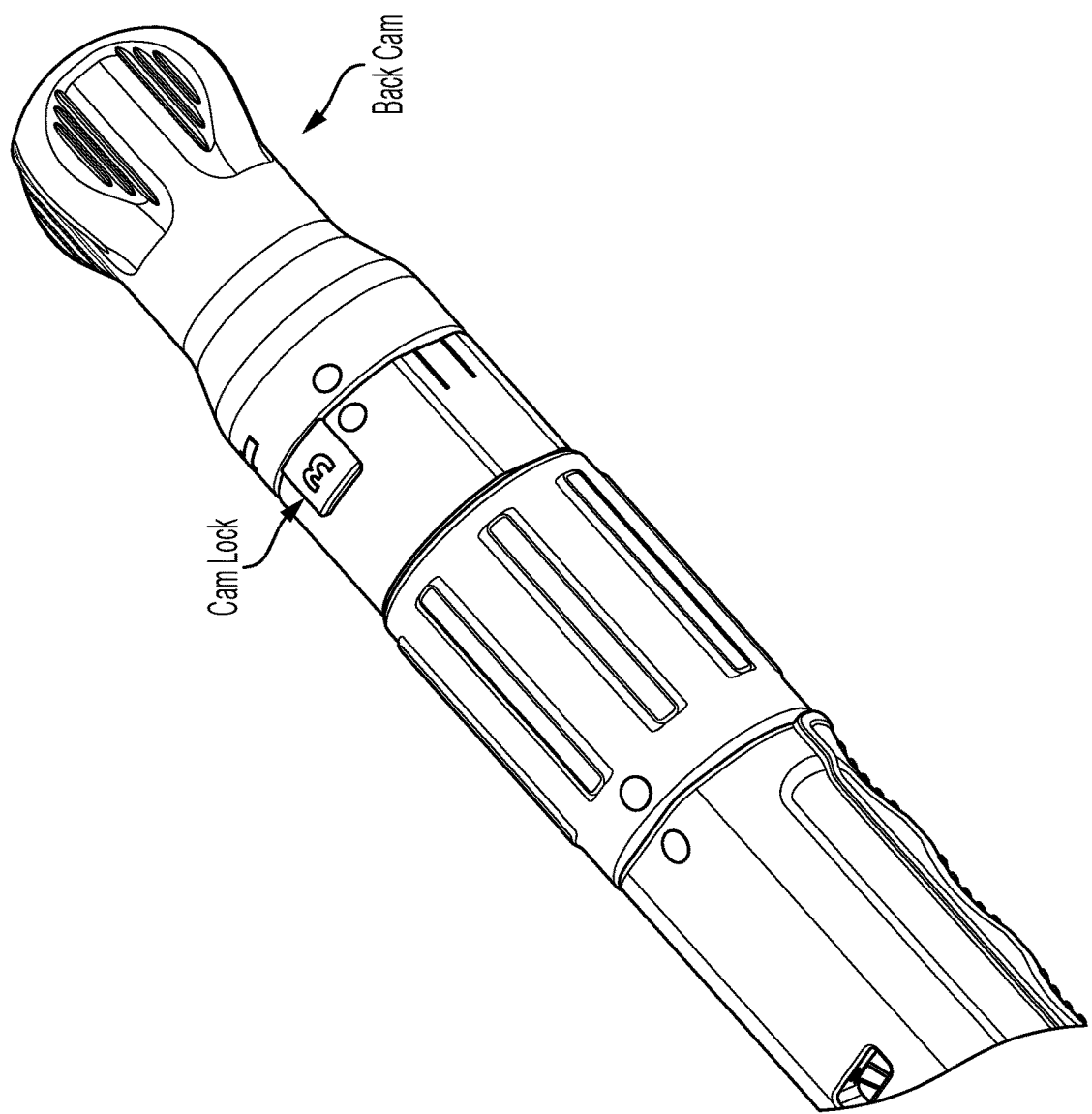
FIG. 18 depicts an image of a device assembly, wherein the back cam is rotated clockwise 180°.

In certain embodiments, the handle end houses the release sleeve hub, the retainer sleeve hub, and the push tube hub (see FIG. 16). In certain embodiments, the retainer sleeve hub remains stationary while (a) the push tube hub moves forward, which deploys a retention member (e.g., a pin), and (b) the release sleeve hub moves back to release the implant. In certain embodiments, these hub movements are actuated by depressing the cam lock (3) and rotating the back cam (4) clockwise 180° from a first position (see FIG. 17) to a second position (see FIG. 18). In certain embodiments, the hub movements, e.g., depressing the cam lock (3) and rotating the back cam (4), can be actuated only after the guidewire is fully retracted from the device. In certain embodiments, the hub movements, e.g., depressing the cam lock (3) and rotating the back cam (4), can be actuated without the guidewire fully retracted from the device. In certain embodiments, the delivery shaft and/or handle comprise a plurality of graphical markings and/or engravings (e.g., alphanumeric markings) indicative of an actuating sequence for use of the device (e.g., numbering to guide the user in the use of the device).

Exemplary Applications of the Methods and Devices

The methods and devices described herein, e.g., the delivery system design and its variants, can provide a system for the delivery of an implant from its assembly through transportation and storage, and ultimately during all stages of implant deployment into an aperture in a hollow vessel, e.g., an opening in a vessel wall that the implant is intended to seal. An exemplary implant is described hereinbelow and in U.S. patent application Ser. No. 13/781,628, which is incorporated by reference in its entirety.

Using the methods and devices described herein, an implant can be delivered through an introducer sheath into a hollow vessel (such as an artery or a vein) within which there had been made an access hole to perform a minimally invasive procedure. In certain embodiments, during this delivery and deployment of the implant, the graduated sheath in conjunction with the blood signaling dilator can provide a positional indication of the implant. Exemplary applications of the methods and devices described herein include: Closing access site holes in hollow vessels; closing access site holes in blood vessels; closing holes in arteries or veins; closing small and large holes up to 30 F in hollow vessels; closing access site holes in the abdominal cavity post endoscopic procedures; or closing access site holes in the femoral artery, subclavian artery, ascending aorta, axillary and brachial arteries.

The methods and devices described herein include a system for delivering an implant in the correct positional location during closure of holes in a blood vessel, and a tool to successfully deliver an implant to close large holes in blood vessels in patients who have diseased vessels and who may have plaques and/or calcified lesions near the access site.

Exemplary Implants

In certain embodiments, an implant comprise a foot including a distal portion configured to be disposed distally beyond a distal surface of the tissue when the device is in a sealing position, and a proximal portion configured to extend proximally through the aperture and proximally beyond a proximal surface of the tissue when the device is in the sealing position; a flexible wing positionable against the distal surface of the tissue adjacent the aperture such that the flexible wing is disposed between the anterior distal portion of the foot and the distal surface of the tissue when the device is in the sealing position; and an elongated retention member supported by the proximal portion of the foot, the retention member moveable with respect to the proximal portion from a first position to a second position such that a portion of the tissue is disposed between the retention member and the flexible wing when the device is in the sealing position.

Figure 19A:
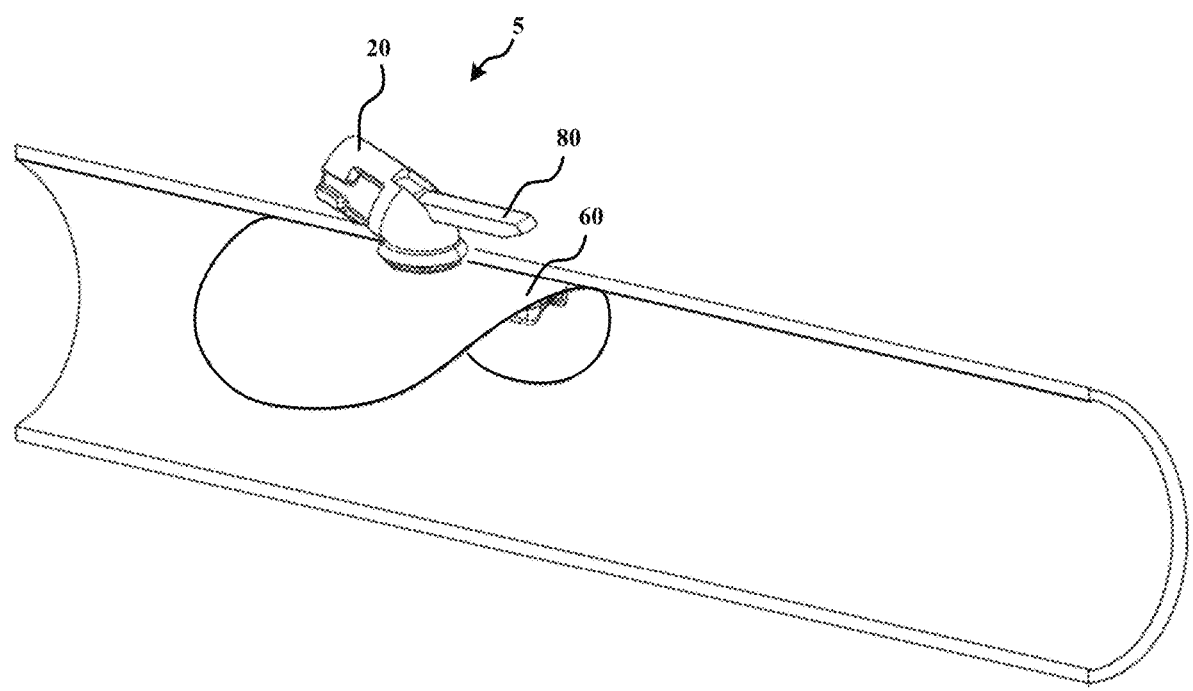
FIG. 19A shows a perspective view of a closure device with an alternative extra-luminal pin and situated on a guidewire extending into an artery, the artery shown in cross-section.
Figure 19B:
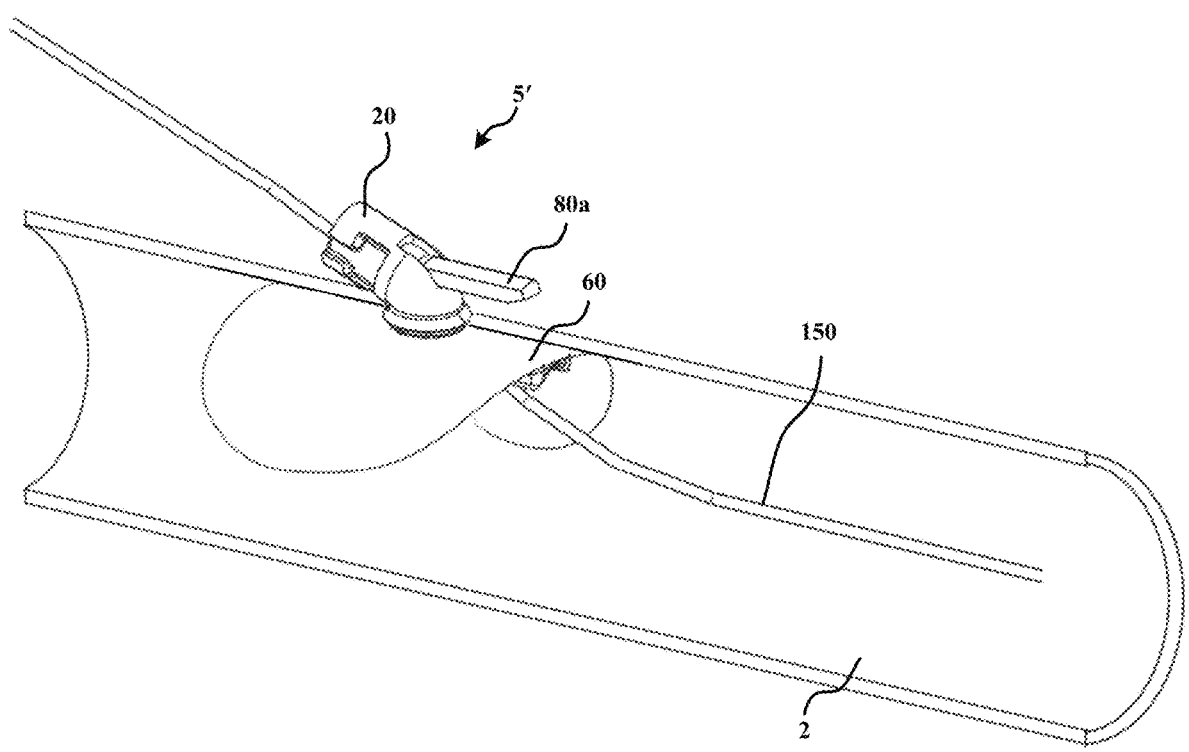
FIG. 19B shows a perspective view of the closure device of FIG. 19A with an alternative extra-luminal pin and situated on a guidewire extending into the artery of FIG. 19A, the artery shown in cross-section.
Figure 19C:
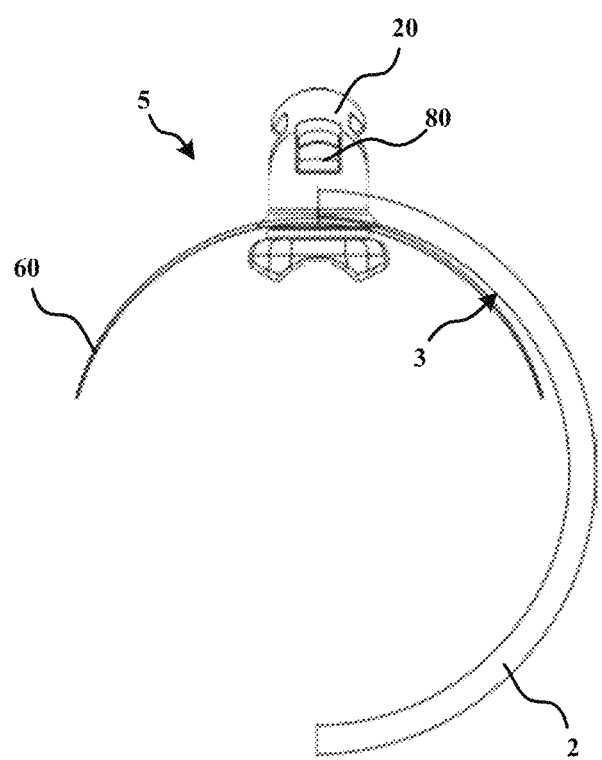
FIG. 19C shows a front view of the closure device of FIG. 19A engaging the artery, the artery shown in cross-section.

In certain embodiments, implant device components (e.g., the foot core 20, the flexible wing 60, and the extra-luminal pin 80, 80a in the illustrated examples of FIG. 19A to 19C) are manufactured from synthetic absorbable materials, although other suitable non-synthetic and/or non-absorbable materials may be used instead of, or in addition to, these synthetic absorbable materials. The flexible wing 60, the foot core 20, and the extra-luminal pin 80, 80a may each be manufactured from any suitable material, e.g., Polydioxanone (PDO), Poly-L-lactide (PLLA), Poly-D-lactide (PDLA), blend of D-lactide and L-lactide, i.e. poly-DL-lactide (PDLLA), Polyglycolide (PGA), blend of Poly-L-lactide and Polyglycolide (PLGA), ε-Caprolactone, Poly (ethylene glycol) (PEG), magnesium alloy, 3-hydroxypropionic acid, Polyanhydrides, poly(saccharide) materials or combinations of these. It should be appreciated, however, that any one or more of the components of the implant device 5, 5' may be formed of any suitable material. Moreover, some or all of the components of the device 5 may be made of the same or different materials relative to each other. The flexible wing may be manufactured as a thin sheet, it may also be made of a woven material, e.g., using electrospinning, weaving and knitting processes.

FIGS. 19A to 19C represent each of these components in situ. The arteriotomy seal is achieved in large part by the hydraulic haemodynamic pressure, which acts on the flexible wing 60 to force the flexible wing 60 against the luminal surface and conform to the luminal topography to seal around the arteriotomy.

FIGS. 20A to 20D show the assembled implant 5 showing three components—foot core 20, flexible wing 60, and extra-luminal pin 80. Although the example illustrated in FIGS. 20A to 20D consists of three pieces, it should be appreciated that more or few pieces may be provided. For example, the flexible wing 60 may be integrally formed with the foot 20 as a single, monolithic piece.

Figure 20A:
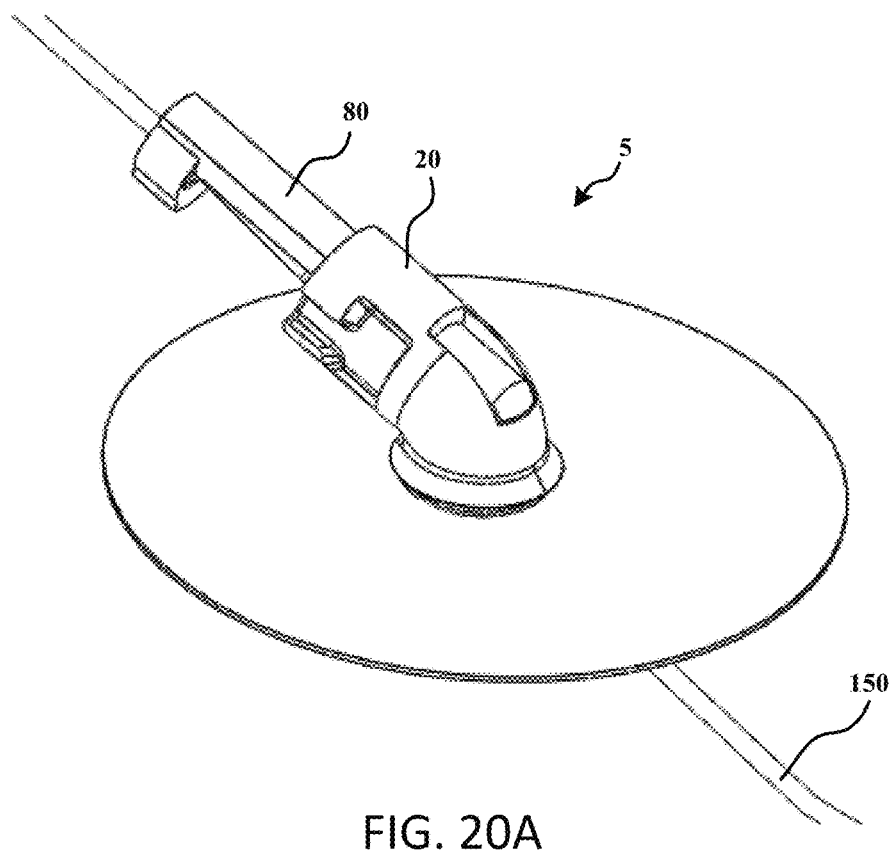
FIG. 20A shows a perspective view of the closure device of FIG. 19A when not engaged with the artery, disposed on a guidewire, and with an extra-luminal pin in a retracted position.
Figure 20B:
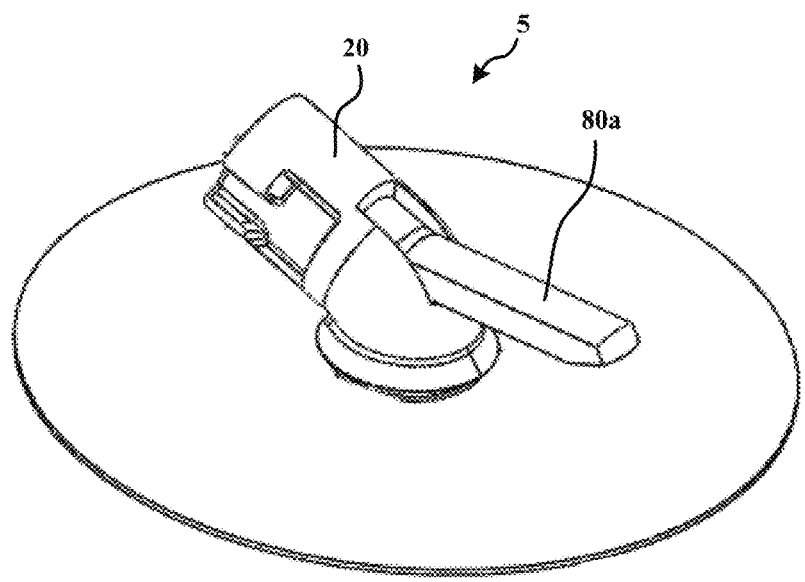
FIG. 20B shows a perspective view of the closure device of FIG. 20A when not engaged with the artery, and with the extra-luminal pin in a deployed position.
Figure 20C:
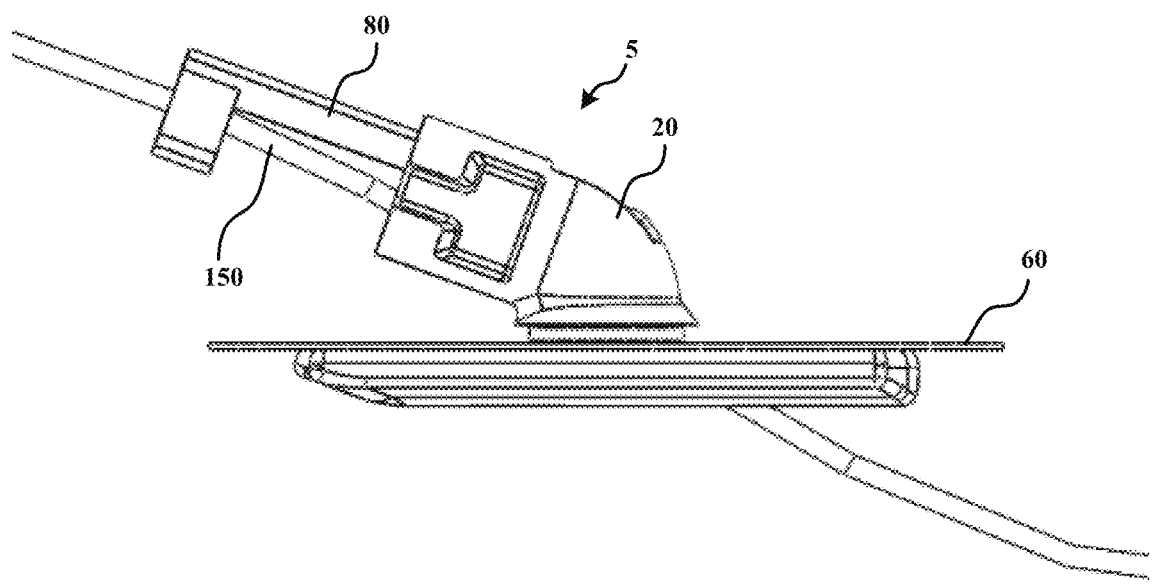
FIG. 20C shows a right side view of the closure device shown in FIG. 20A.
Figure 20D:
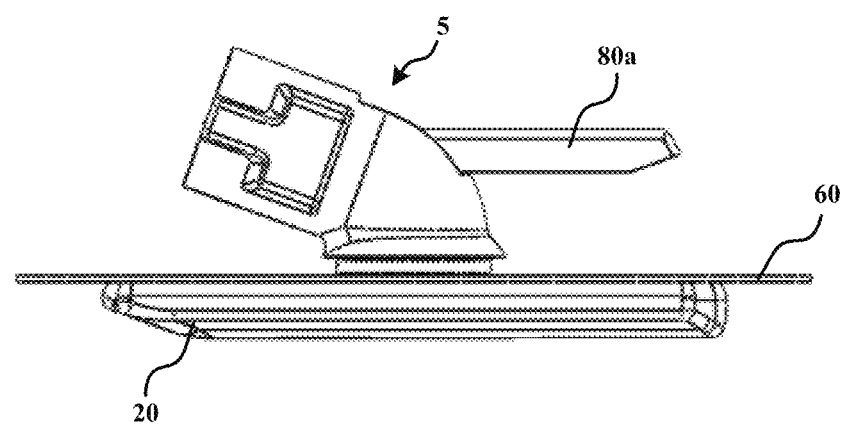
FIG. 20D shows a right side view of the closure device shown in FIG. 20B.
Figure 21A:
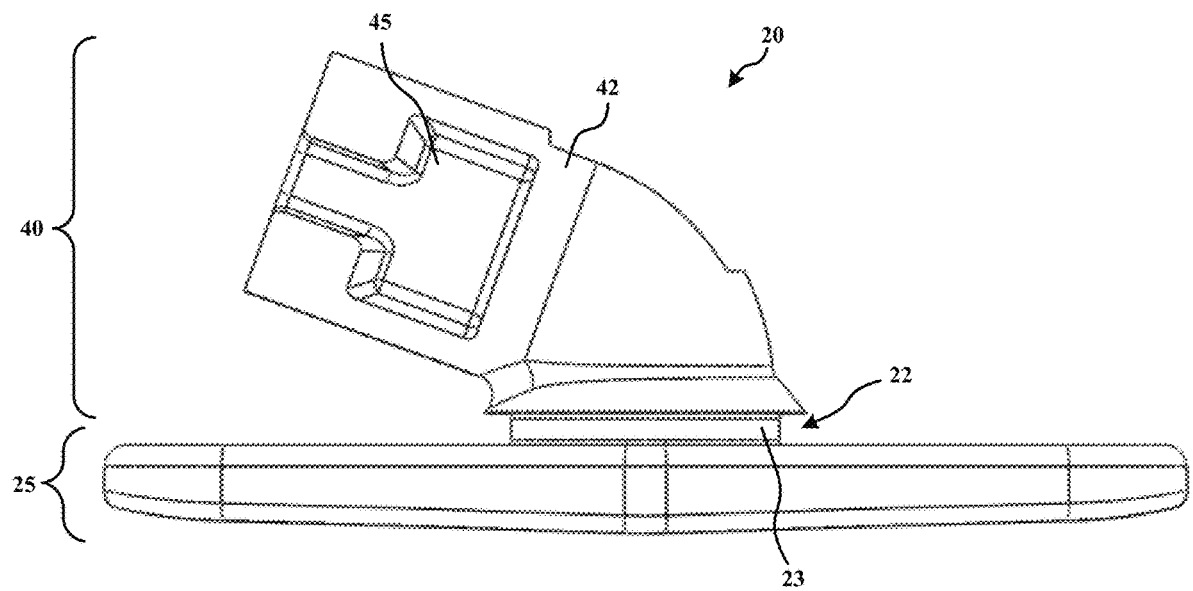
FIG. 21A shows a right side view of a foot core of the closure device shown in FIG. 1A.
Figure 21B:
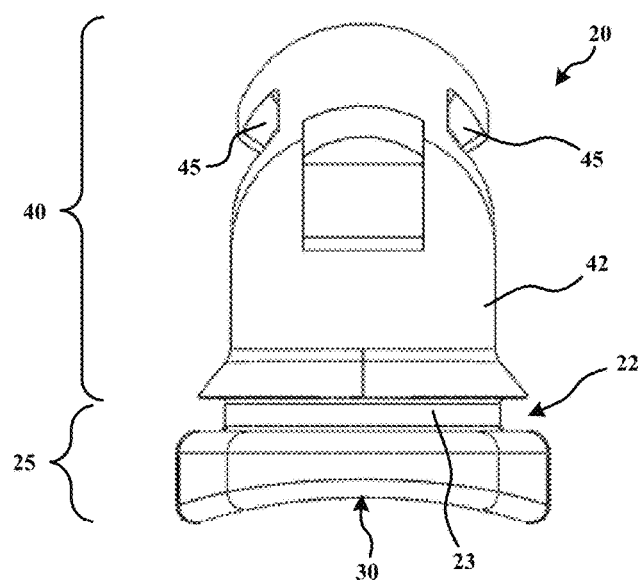
FIG. 21B shows a front view of the foot core shown in FIG. 21A.
Figure 21C:
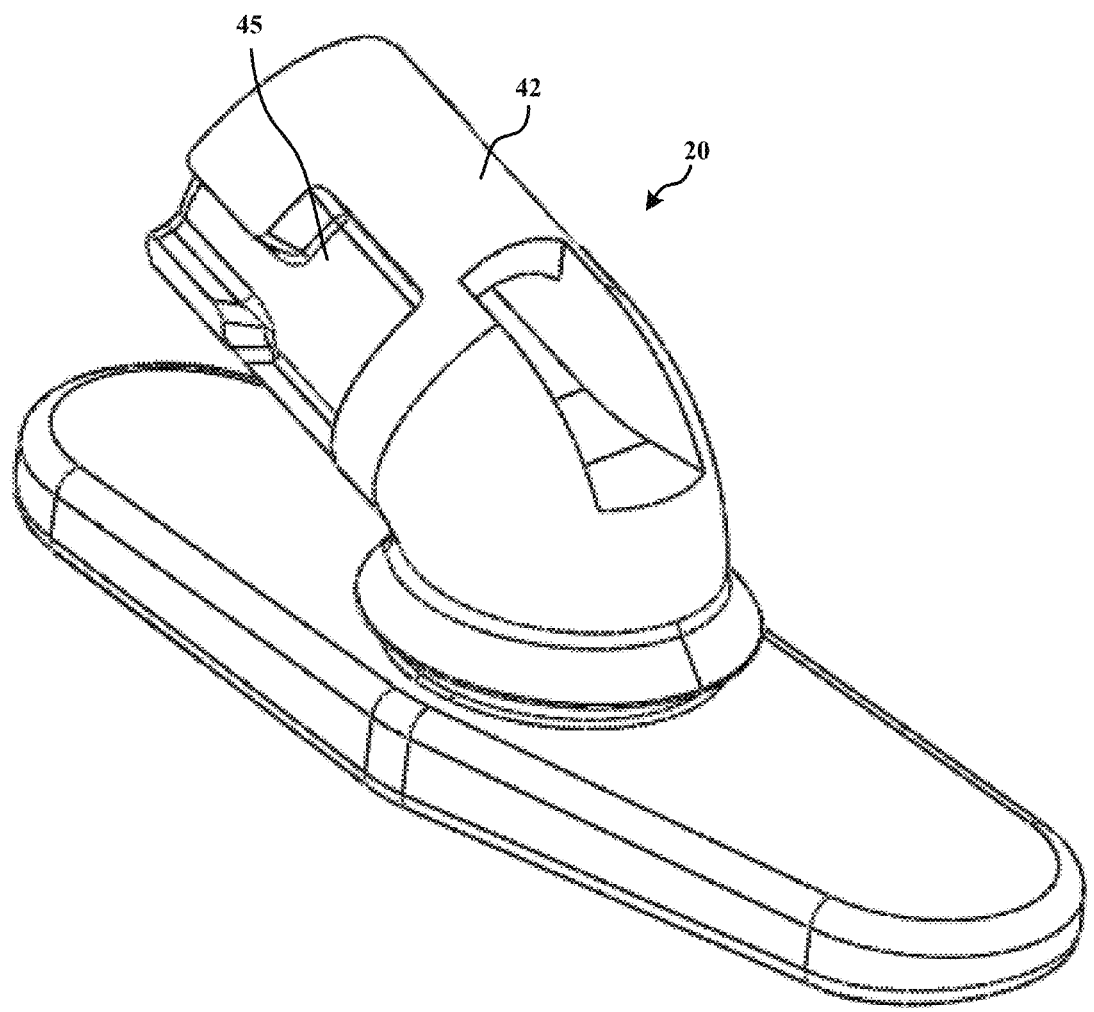
FIG. 21C shows a perspective view of the foot core shown in FIG. 21A.
Figure 21D:
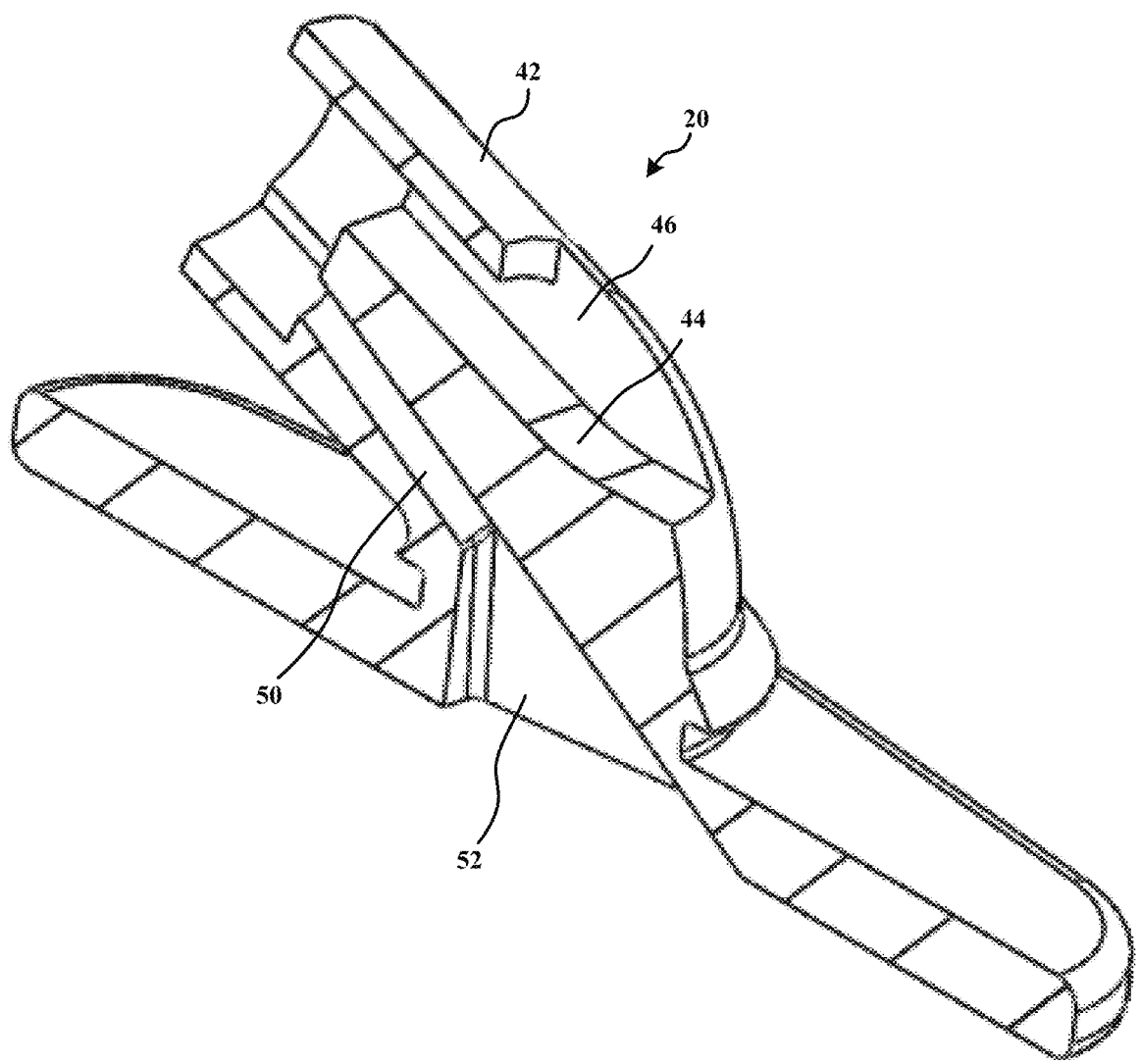
FIG. 21D shows a cross-sectional perspective view of the foot core shown in FIG. 21A.
Figure 22A:
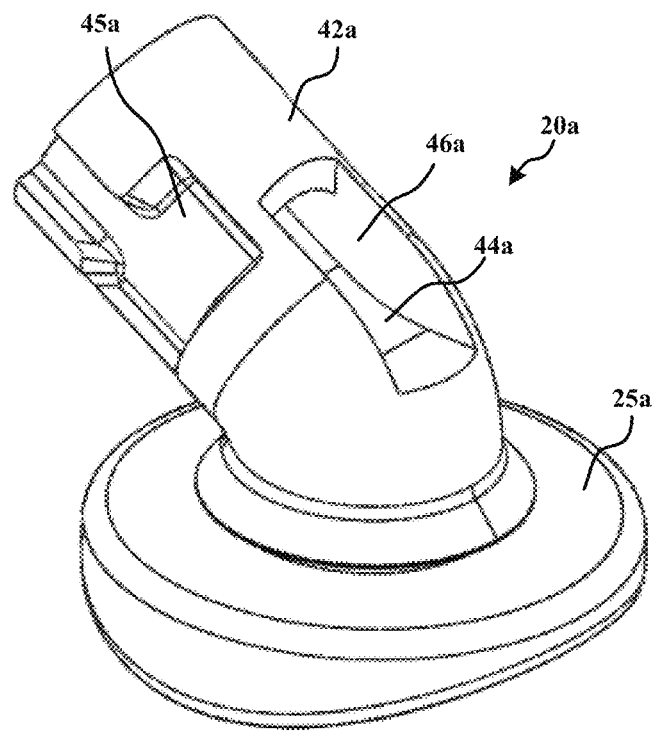
FIG. 22A shows a perspective view of another foot core.
Figure 22B:
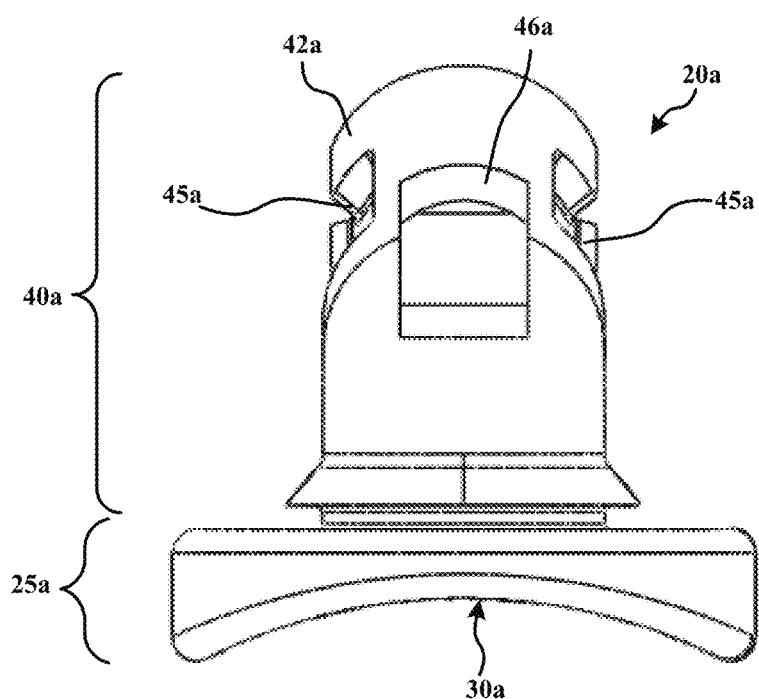
FIG. 22B shows a front view of the foot core shown in FIG. 22A.
Figure 22C:
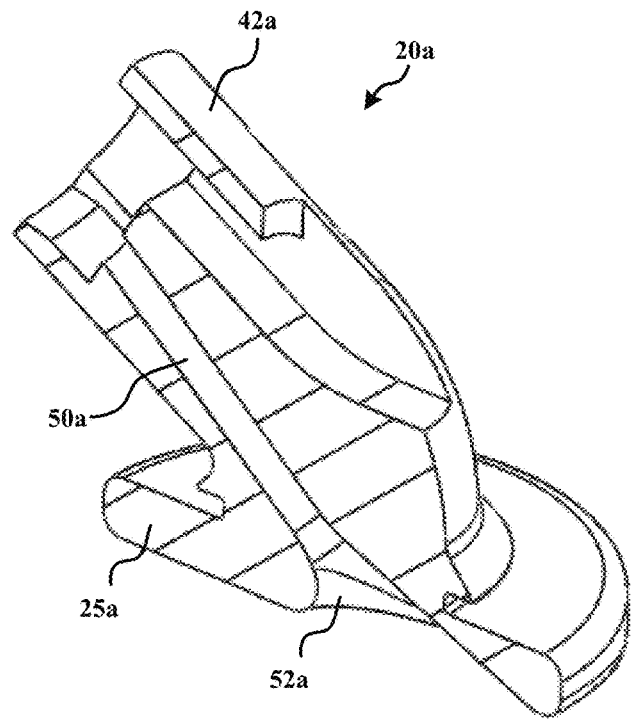
FIG. 22C shows a cross-sectional perspective view of the foot core shown in FIG. 22A.
Figure 22D:
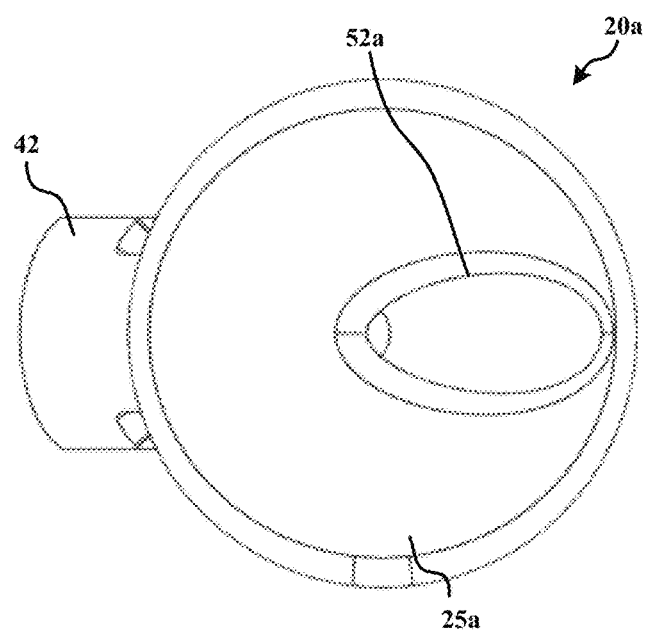
FIG. 22D shows a bottom view of the foot core shown in FIG. 22A.
Figure 22E:
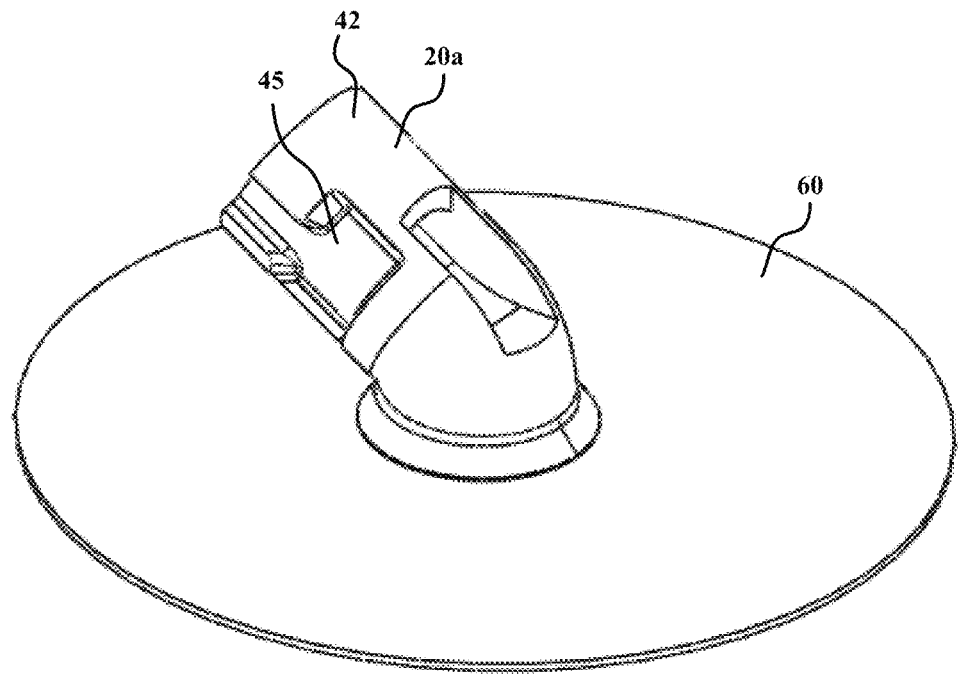
FIG. 22E shows a perspective view of the foot core shown in FIG. 22A and a wing element.
Figure 22F:
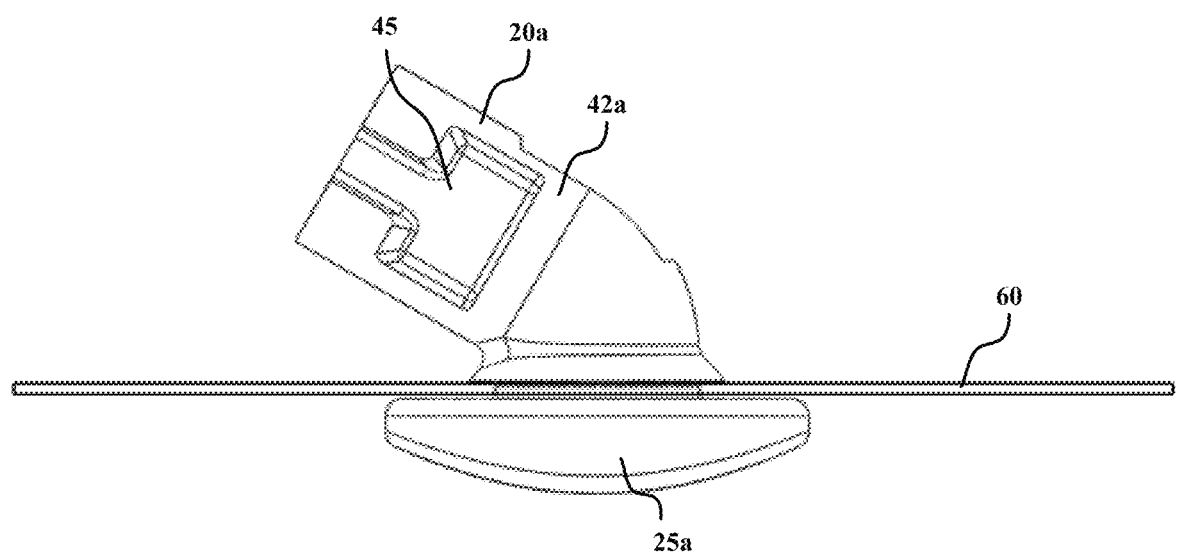
FIG. 22F shows a right side view of the foot core and wing element shown in FIG. 22E.

As illustrated in FIGS. 20A and 20C, a guidewire 150 extends through the implant 5. FIGS. 20B and 20D show the implant 5 after proximal retraction of the guidewire 150 and subsequent extension, or deployment, of the extra-arterial pin 80 to its distal, or deployed, position relative to the foot core 20.

FIGS. 20A and 20C show the implant 5 with the extra-luminal pin 80 in a retracted or undeployed state, and FIGS. 20B and 20D show the extra-luminal pin 80 in a distally extended or deployed state.

Referring, for example, to FIGS. 21A to 21D, the foot core 20 includes both an intra-luminal section 25 which is configured to be maintained in the interior of the artery 2, or other tissue structure, when the implant 5 is in situ, and an extra-luminal section 40 which passes through the arteriotomy across the arterial wall when the implant 5 is in situ. The intra-luminal section 25 and the extra-luminal section 40 are separated at a recess 22, which is configured to receive the wing 60 such that a cylindrical recessed surface 23 is maintained inside a circular central cut-out or aperture 65 in the wing 60. The aperture 65 is illustrated, for example, in FIGS. 24A and 24B.

It is noted that since some illustrated examples are provided in the context of an arteriotomy, the terms "intra-luminal" and "extra-luminal" may be referred to as "intra-arterial" and "extra-arterial" in the context of the illustrated embodiments, it being understood that the arteriotomy-closure application is non-limiting and the closure of any suitable tissue aperture may be performed by example embodiments of the present invention.

The extra-luminal section 40 of the foot core 20 is provided in the form of a neck 42 which extends from the intra-luminal section 25 at an angle, e.g., selected from a range from 10° to 70°, and has five primary functions:
1. Secure the flexible wing 60 within the recessed section 22. This recessed section 22 also provides an effective seal between the flexible wing 60 and foot core 20. In the example illustrated, e.g., in FIGS. 19A to 19C, the flexible wing 60 is free to rotate within this recess 22. It should be understood, however, that the engagement of the wing 60 in the recess 22 may be provided such that the wing 60 is not rotatable within the recess 22.
2. Secures and allows release of the entire implant to a delivery system via interlock recesses 45 in the neck 42. This functionality is described in further detail elsewhere herein.
3. Houses 46 the extra-luminal pin 80 and secures it when deployed to its final position.
4. Houses a guidewire channel or conduit 50. The guidewire channel 50 is illustrated, e.g., in FIG. 21D.
5. The 10°-70° incline on the neck in combination with the extra-luminal pin 80, or 80a, also provides, e.g., for safety purposes, protection against the implant being pushed off the luminal surface by application of extracorporeal pressure above the implantation site or due to patient movements.

The intra-luminal section 25 of the foot core 20 has a primary function to provide a rigid scaffold to support the flexible wing 60. The underside of the intra-luminal section 25 may be concave in cross-section to reduce its profile within the artery 2 and has a hollow entry portion or port 52 of the guidewire channel 50 adjacent the neck 42, shown in the sectioned foot core 20 of FIG. 21D.

FIGS. 22A to 22F show another foot core 20a. This configuration has a circular intra-luminal portion 25a in plain view and a concave surface 30a which is concave in cross-sectional profile within the artery 2.

Figure 23A:
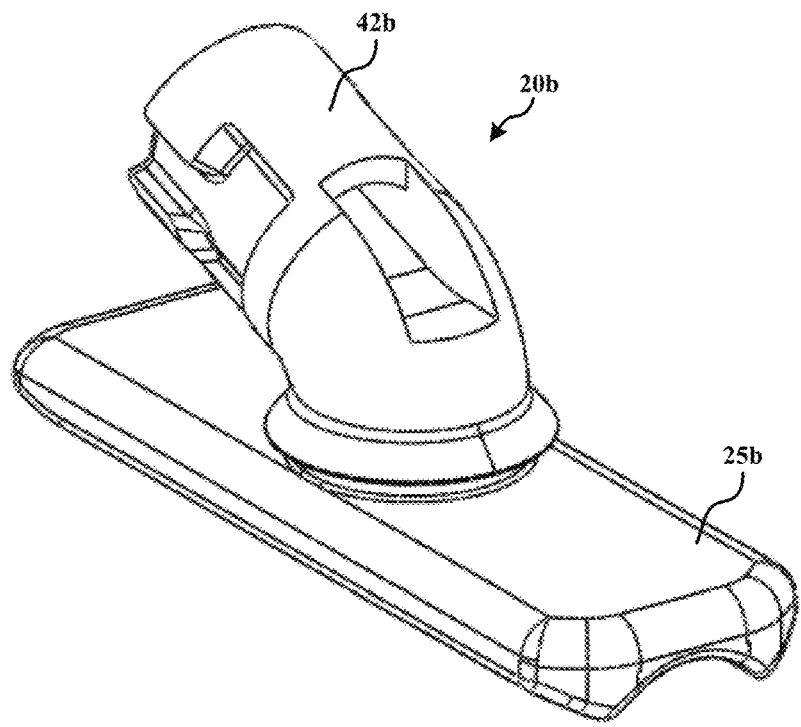
FIG. 23A shows a perspective view of another foot core.
Figure 23B:
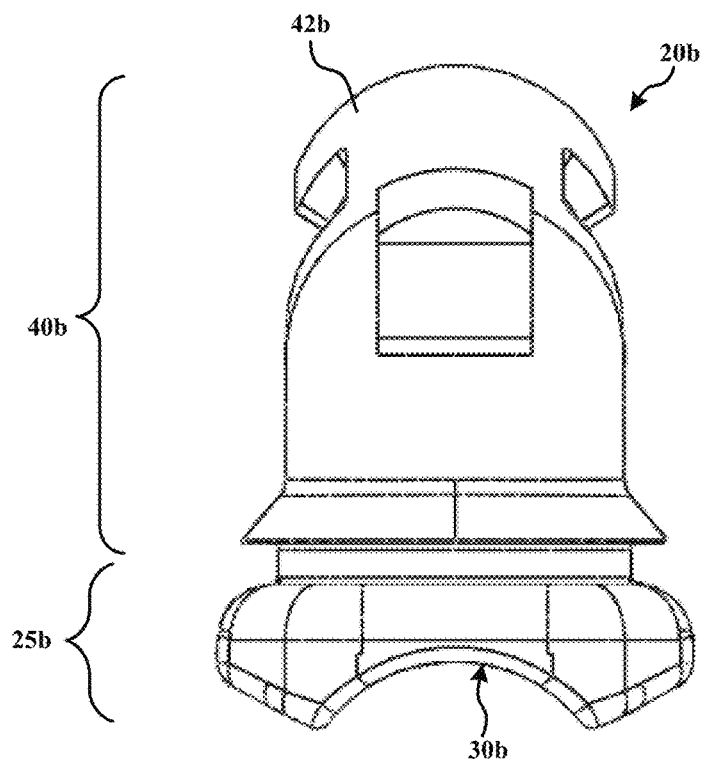
FIG. 23B shows a front view of the foot core of FIG. 23A.

It should be appreciated that many variations of the intra-luminal portion may be provided, only a limited number of which are shown herein. For example, FIGS. 23A to 23B show another foot core 20b having an intra-luminal portion 25b that is generally rectangular in plain view and includes a concave bottom surface.

Figure 24A:
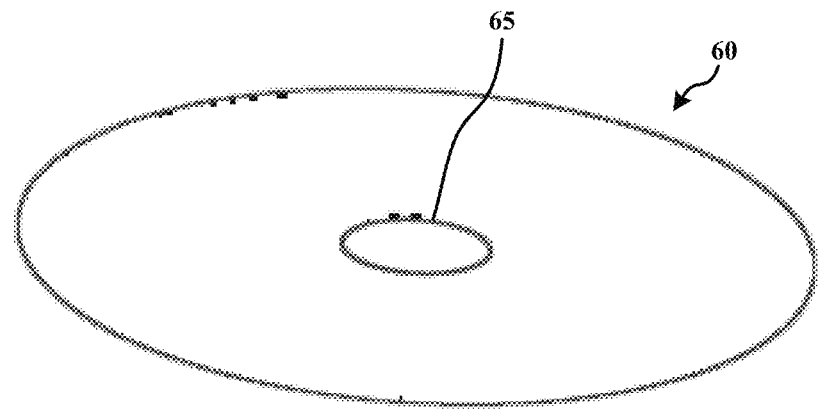
FIG. 24A shows a wing element of the device of FIG. 19A in a flat state.
Figure 24B:
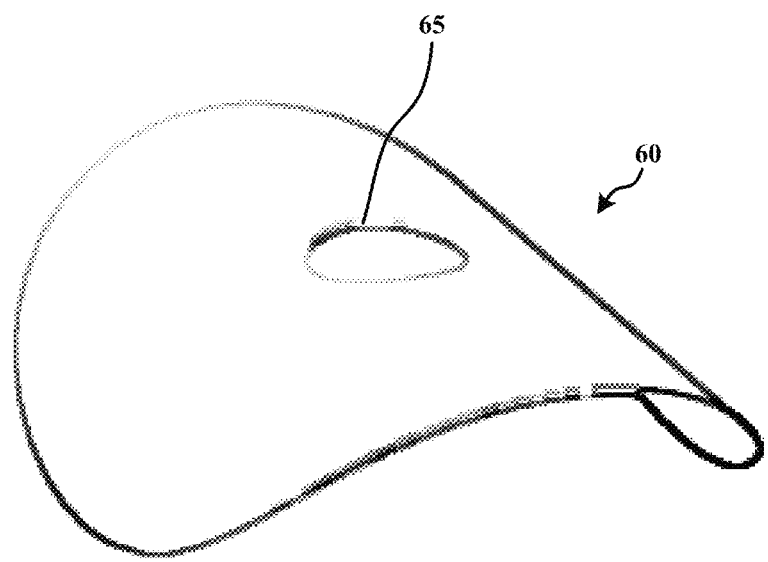
FIG. 24B shows the wing element of FIG. 24A in a folded or curved state.

The flexible wing 60, FIGS. 24A and 24B, is a thin disc sized to be larger than the arteriotomy diameter (arteriotomy diameter is equivalent to the outer diameter of the delivery/procedural sheath 100). The central hole 65 and disc portion are circular in shape, in plain view. It should be understood, however, that other geometries may be provided for the hole and/or the disk portion of the wing 60. The central hole 65 is sized to accept recessed cylindrical surface 23 within the foot core 20's flexible-wing retention recess 22 shown, e.g., in FIGS. 21A and 21B, and is free to rotate relative to the foot core 20 about the concentric axis of the recessed cylindrical surface 23.

FIG. 24A shows the flexible wing 60 in its flat and relaxed state, and FIG. 24B shows the flexible wing 60 in its curved state, which corresponds to the final configuration within the artery 2. The curvature of the wing 60 shown in FIG. 24B corresponds to the curvature of the interior of the artery to which the wing 60 conforms in its final implanted state. When implanted, the wing 60 is pressed against the artery interior wall by hemodynamic hydraulic pressure exerted by the blood in the artery 2. Although the wing 60 is flat, or planar, in its relaxed state, it should be appreciated that the wing 60 may be curved or have any other suitable geometry in its relaxed state.

Referring, e.g., to FIGS. 19A to 19C, the flexible wing 60 is positioned within the artery 2 against the luminal surface 3 adjacent the arteriotomy and held in this position with the aid of the hemodynamic hydraulic pressure it acts as the primary seal around the arteriotomy to control bleeding. Referring to FIG. 19C, the wing 60 is illustrated slightly pulled away from the luminal surface 3 only to facilitate illustration.

In addition to elastically deforming to conform to the luminal surface 3 of the artery 2, the flexible wing 60 also elastically deforms to fit within the procedural sheath 100 for delivery into the artery 2. This is achieved by rolling the wing 60 into a cylinder-like configuration. Once within the artery 2, and beyond the procedural sheath 100, the flexible wing 60 intrinsically recovers towards its flat state to allow the hemodynamic hydraulic pressure in the artery 2 to conform the wing 60 to the shape of the arterial luminal and surface topography 3. In this regard, the elasticity of the wing 60 allows the wing 60 deform locally at differing areas of the luminal surface 3 of the artery 2. This allows the wing 60 to conform to local irregularities along the surface 3 to ensure that the arteriotomy is adequately sealed despite such irregularities.

The flexibility of the wing 60 is not just important in a lateral configuration to facilitate collapse during delivery, but it is also important to flex in a longitudinal plane. Flexibility in both lateral and longitudinal planes is important to ensure an effective seal around the arteriotomy of arteries in differing disease states with different surface topographies and varying anatomical configurations. Longitudinal flex is facilitated by the configurations shown, e.g., in FIGS. 20A-23D, by the flexible wing 60 and the foot core 20 being separate and distinct parts that are non-fixedly mated together. For example, since the wing 60 is not fixed to the foot 20, it is able to separate from the upper surface of the relatively rigid intra-luminal portion 25 of the foot core 20 at regions where the topography of the arterial surface 3 deviates or is disposed at a greater distance from the upper surface of the intra-luminal portion 25 than at adjacent regions of the surface 3.

Although the wing 60 has a circular outer periphery, it should be understood that the wing 60 may be provided with any suitable geometry. Further, although the wing 60 has a uniform thickness, it should be understood that the wing 60 may be provided with a thickness that varies at different regions of the wing 60. For example, the wing 60 could have a thickness in its central region that is greater than a thickness toward the circumferential periphery of the wing 60.

Figure 25A:
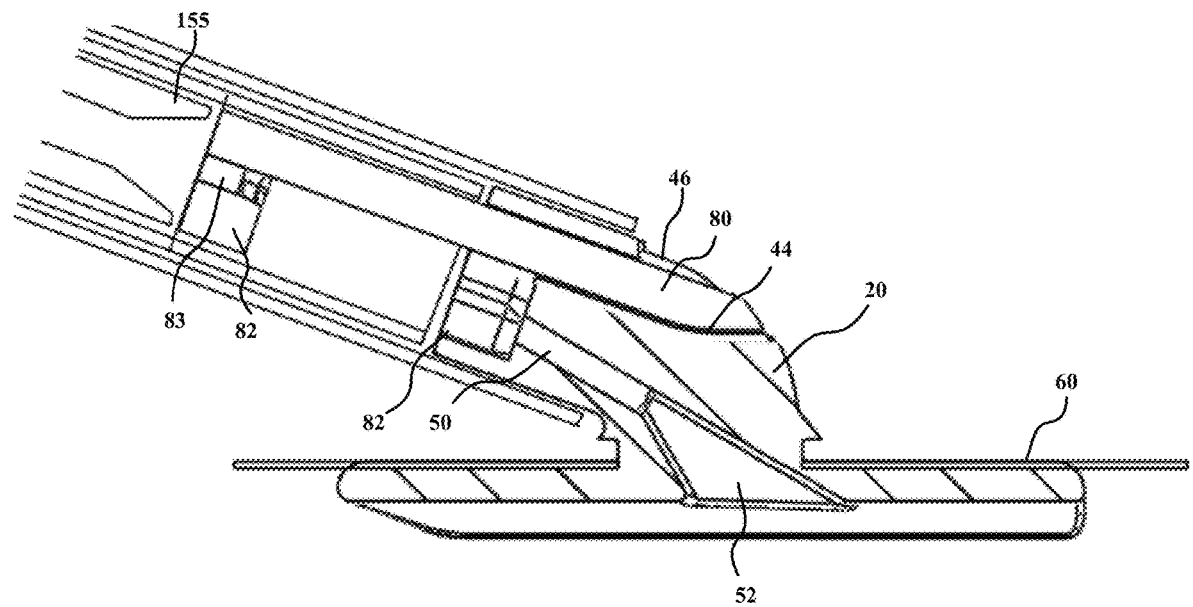
FIG. 25A shows a cross-sectional right side view of a closure system incorporating the closure device shown in FIG. 19A.
Figure 25B:
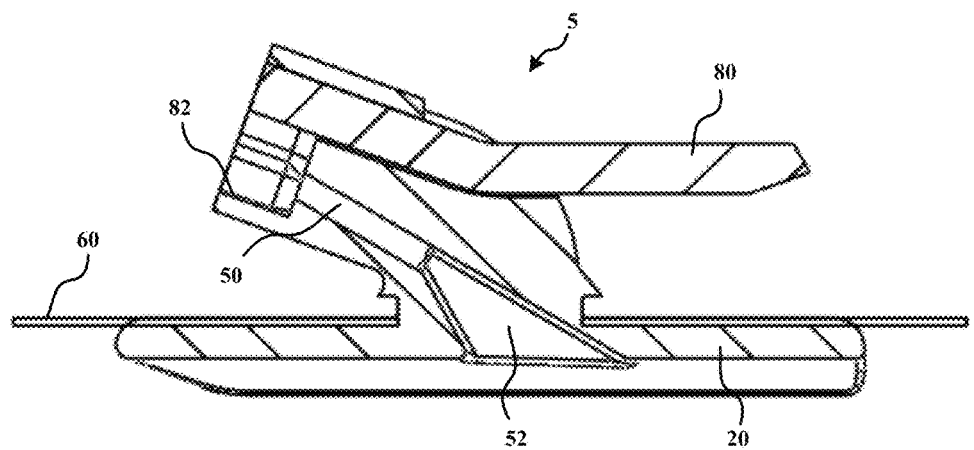
FIG. 25B shows a cross-sectional right side view of the closure device shown in FIG. 25A in a released state.

FIGS. 25A and 25B shows an assembled implant 5 in cross section. FIG. 25A shows the implant 5 in a state where the guidewire 150 would be in situ. FIG. 25B shows the deployed implant 5.

The extra-luminal pin 80 is a safety feature of the closure system to prevent the implant being pushed off the luminal surface by application of extracorporeal pressure above the implantation site or due to patient movements. The extra-luminal pin 80 in the illustrated example does not generally contribute to or form part of the sealing function of the implant 5. The implant 5 will seal the arteriotomy in the absence of the extra-luminal pin 80 in accordance with some example embodiments. The extra-luminal pin 80 is deflected parallel to the artery 2 wall as it is advanced, as illustrated, e.g., in FIG. 25B. This deformation of the extra-luminal pin 80 helps secure it in its post deployment position. The pin 80 is also maintained in this position via a press fit between the proximal portion 82 of the pin and the proximal recess 44 of the foot core 20 into which the proximal portion 82 is pressed.

Figure 25C:
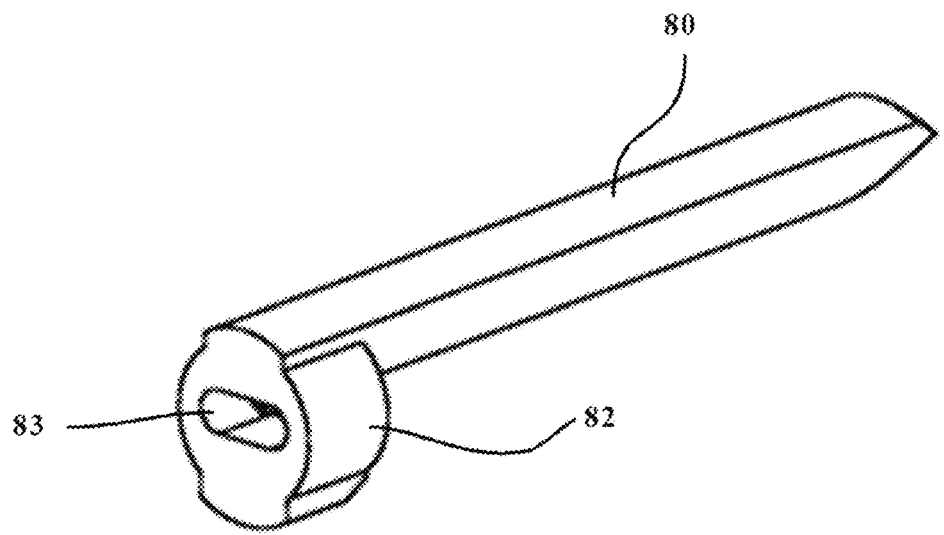
FIG. 25C shows a perspective view of the extra-luminal pin element.

Depending on implant design and requirements, the extra-luminal pin 80 may also be used to occlude the guidewire hole within the foot core 20 when deployed, e.g., in a configuration such as illustrated in FIGS. 25A and 25B, the pin 80 being illustrated in isolation in FIG. 25C. When deployed, as illustrated, e.g., in FIG. 25B, an enlarged proximal portion 82 of the extra-luminal pin 80 blocks the guidewire channel 50. In its proximal or retracted position, the pin 80 allows the guidewire 150 to pass through channel 83 in the enlarged proximal portion 82. When the pin 80 is moved into its distal or deployed position, the channel 83 does not align with the channel 50 in the foot core 20, thereby blocking the channel 50. In the proximal or retracted position, the guidewire is able to pass through both channels 50 and 83 since the channels 50 and 83 are sufficiently axially spaced apart.

It should be understood, however, that any other suitable mechanism may be provided for closing the guidewire channel 50. For example, again referring to FIGS. 25A and 25B, the formation of coagulated blood in the conically shaped entry portion 52 of the guidewire channel 50. The coagulated blood would then be pressed and locked into the narrowing conical geometry of the entry portion 52 by the hydraulic pressure exerted by the blood in the artery 2. To facilitate coagulation of the blood in the entry portion 52, the guidewire 150 may be left in place for, e.g., several minutes (e.g., 4 to 5 minutes). The presence of the guidewire may, during this period, induce sufficient clotting of the blood to form the closure in the entry portion 52. Then, upon retraction of the guidewire 150, the coagulated blood would compress and collapse to fill the void left by the removal of the guidewire 150.

Figure 25D:
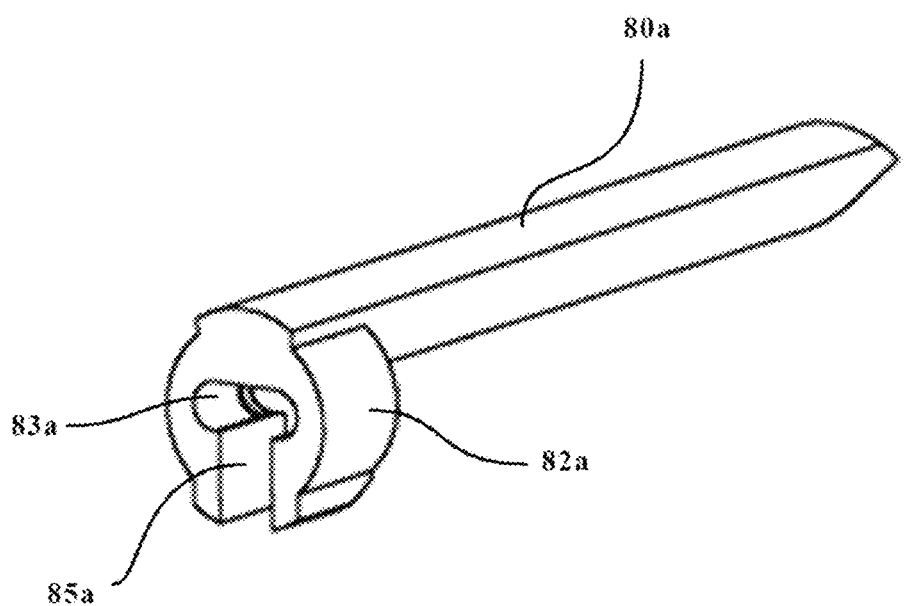
FIG. 25D shows a perspective view of another extra-luminal pin element.

Although the illustrated entry portion 52 of the guidewire channel 50 is conical, it should be appreciated that any suitable geometry may be provided. Referring to FIG. 25D, an alternative extra-luminal pin 80a is shown with an additional slot 85a to facilitate the pin 80a being moved into its distal or extended position whilst the guidewire 150 remains in place.

In a manner analogous to that of the device 5 illustrated, e.g., in FIGS. 25A and 25B, the pin 80y may be used to occlude the guidewire hole within the foot core 20y when deployed.

Advantages

Advantages of the methods and devices described herein include the following. In certain embodiments, a loading funnel aligns an implant for loading into a loading cannula. In certain embodiments, an implant is loaded during device removal from the packaging tray. In certain embodiments, a short device reduces potential for movement whilst achieving tamponade, resulting in faster deployment times. A user can position a hand on the patient during use, thus experiencing less fatigue. In certain embodiments, rotational actuations are employed to deploy the device. In certain embodiments, a custom made introducer can be supplied in varying French sizes with the device, which can enable device to be used to close various size holes in arteries or veins. In certain embodiments, a blood signal on the dilator in conjunction with graduations on the introducer shaft provides the user with an indication of tissue tract depth, which is utilized in identifying the positional location of the implant for achievement of tamponade and subsequent deployment of the implant. The methods and devices described herein can provide an indication to the user when to expect tactile feel when achieving tamponade during deployment. In certain embodiments, less force is required to load the device into its delivery profile (i.e., reducing its cross-sectional profile in preparation for delivery) as the loading cannula internal diameter is enlarged. The methods and devices described herein can reduce the chance of accidental pull-out of the implant as the user is aware of, e.g., the arteriotomy or other vessel (e.g., a vein) access location.

What is claimed is:

1. A device for sealing an aperture in a hollow vessel of a tissue, the device comprising:
   a. an implant configured to seal the aperture when positioned adjacent to the aperture, the implant comprising a retention member and a flexible wing; and
   b. a delivery shaft configured to engage the implant to allow the implant to be maneuvered into sealing engagement with a distal surface of the tissue, the delivery shaft comprising:
      (i) a retaining sleeve comprising a locking projection engageable with a locking recess of the implant to secure the implant to the delivery shaft;
      (ii) a release sleeve axially slideable relative to the retaining sleeve between a first axial position in which the release sleeve is configured to maintain locking engagement between the locking recess of the implant and the locking projection of the retaining sleeve, and a second axial position in which the release sleeve permits the locking projection of the retaining sleeve to disengage the locking recess of the implant; and
(iii) a handle coupled to the delivery shaft, comprising;
(a) a sheath cam moveable between a first position and second position relative to the handle, (b) a sheath carriage connected to a sheath and (c) a back cam at a proximal end of the handle,
wherein the device is configured such that rotational movement of the sheath cam from the first position to the second position causes (x) movement of the sheath carriage relative to the handle, causes (y) the movement of one end of the sheath into the handle, and causes (z) exposure of the implant in the vessel in an atraumatic way,
wherein the back cam is configured such that a rotational movement of the back cam from a first position to a second position actuates deployment of the retention member and actuates the release sleeve to release the implant from the retaining sleeve, such that a portion of the tissue is disposed between the retention member and the flexible wing when the implant is in a sealing position,
wherein the handle further comprises a cam lock that prevents the rotational movement of the back cam when the cam lock is not depressed, and that releases the back cam when the cam lock is depressed, thereby allowing the rotational movement of the back cam, and
wherein the cam lock is located on a surface of the handle enabling a user to depress the cam lock to allow rotational movement of the back cam.

2. The device according to claim 1, wherein the locking projection is one of plurality of interlocking projections configured to engage a respective plurality of interlocking recesses of the implant.

3. The device according to claim 1, wherein the locking projection is biased toward a flared position such that movement of the release sleeve from the first axial position to the second axial position causes the interlocking projection to flare away from and out of engagement with the locking recess of the implant.

4. The device of claim 1, wherein the device is configured such that rotational movement of the back cam from the first position to the second position causes (a) a change in the position of two components of the implant relative to each other, and causes (b) the delivery shaft to release the implant.

5. The device of claim 1, wherein the delivery shaft and/or handle comprise a plurality of graphical markings and/or engravings, indicating an actuating sequence for use of the device.

6. The device of claim 1, wherein the delivery shaft and/or sheath comprise a plurality of graphical markings and/or engravings indicating sheath penetration.

7. The device of claim 1, wherein the implant is formed of a polymer adapted to remain shelf stable and functional for sealing after terminal sterilization.

8. The device of claim 7, wherein the polymer is biodegradable.

9. The device of claim 1, wherein the device is configured to seal a perforation in a hollow vessel.

10. The device of claim 1, wherein the implant includes an intraluminal portion configured to form a seal with the perforation by contacting an intraluminal surface of the hollow vessel.

11. The device of claim 1, wherein the implant includes an extra-luminal portion configured to extend outside the hollow vessel, the delivery shaft being configured to engage the implant via the extra-luminal portion.

12. The device of claim 1, wherein the flexible wing extends outwardly from a base portion.

13. The device of claim 1, wherein the device is configured to be guided over a guidewire.

14. The device of claim 1, wherein the flexible wing has a diameter greater than a diameter of the aperture in the tissue.

15. The device of claim 1, wherein the implant comprises a distal foot portion, the flexible wing, and a recessed surface disposed in the distal foot portion and into which the flexible wing is positioned and crimped to provide an effective fluid seal between the foot portion and the flexible wing.

16. The device according to claim 15, wherein the crimping is achieved using at least one of (a) mechanical, (b) chemical, and (c) thermal methods.

17. The device of claim 1, wherein the implant comprises: the flexible wing; and a foot including a distal portion configured to be disposed distally of the flexible wing when the implant is positioned to seal the aperture and a proximal neck configured to extend away from the aperture and proximally away from the aperture.

18. The device according to claim 17, wherein the distal portion of the foot is configured to reinforce the flexible wing to facilitate sealing of the aperture.

19. The device of claim 1, wherein the implant comprises a base portion and the retention member moveable relative to the base portion between a first position and a second position, wherein the pin in the second position is configured to extend outwardly from the base to provide a safety against the base being fully pushed or pulled distally through the aperture to be sealed.

20. The device of claim 1, further comprising: a loading funnel configured to fold the implant into an elongated folded configuration to permit the wing to pass through a procedural sheath when the delivery shaft maneuvers the implant into a location of the aperture to be sealed.

21. A device for sealing an aperture in a tissue, the device comprising:
a. an implant configured to seal the aperture when positioned adjacent to the aperture; and a delivery device releasably coupleable to the implant such that the delivery device is configured to position the implant adjacent to the aperture, wherein the implant comprises a passageway configured to receive a guidewire to guide the implant to the aperture, the implant configured to seal the passageway after complete removal of the guidewire from the passageway; and
b. a delivery shaft configured to engage the implant to allow the implant to be maneuvered into sealing engagement with a distal surface of the tissue, the delivery shaft comprising:
(i) a retaining sleeve comprising a locking projection engageable with the locking recess of the implant to secure the implant to the delivery shaft;
(ii) a release sleeve axially slideable relative to the retaining sleeve between a first axial position in which the release sleeve is configured to maintain locking engagement between the locking recess of the implant and the locking projection of the retaining sleeve, and a second axial position in which the release sleeve permits the locking projection of the retaining sleeve to disengage the locking recess of the implant; and
(iii) a handle coupled to the delivery device; and (a) a sheath cam moveable between a first position and second position relative to the handle, (b) a sheath carriage connected to a sheath and (c) a back cam at a proximal end of the handle, wherein the device is configured such that rotational movement of the sheath cam from the first position to the second position causes (x) movement of the sheath carriage relative to the handle, causes (y) the movement of one end of the sheath into the handle, and causes (z) exposure of the implant in the vessel in an atraumatic way, wherein the back cam is configured such that a rotational movement of the back cam from a first position to a second position actuates deployment of a retention member of the implant and actuates the release sleeve to release the implant from the retaining sleeve, such that a portion of the tissue is disposed between the retention member and a flexible wing of the implant when the implant is in a sealing position, wherein the handle further comprises a cam lock that prevents the rotational movement of the back cam when the cam lock is not depressed, and that releases the back cam when the cam lock is depressed, thereby allowing the rotational movement of the back cam, and wherein the cam lock is located on a surface of the handle enabling a user to depress the cam lock to allow rotational movement of the back cam.

22. The device of claim 1, wherein the proximal end of the handle houses a release sleeve hub, a retaining sleeve hub, and a push tube hub configured such that the retaining sleeve hub remains stationary while (I) the push tube hub moves forward, deploying the retention member, and (II) the release sleeve hub moves back to release the implant, wherein said hub movements (I) and (II) are actuated by a user depressing the cam lock and rotating the back cam from the first position to the second position.

23. The device of claim 21, wherein the proximal end of the handle houses a release sleeve hub, a retaining sleeve hub, and a push tube hub configured such that the retaining sleeve hub remains stationary while (I) the push tube hub moves forward, deploying the retention member, and (II) the release sleeve hub moves back to release the implant, wherein said hub movements (I) and (II) are actuated by a user depressing the cam lock and rotating the back cam from the first position to the second position.

* * * * *